United States Patent
Goodwin et al.

(10) Patent No.: US 6,355,779 B1
(45) Date of Patent: Mar. 12, 2002

(54) CYTOKINE DESIGNATED 4-1BB LIGAND ANTIBODIES AND HUMAN RECEPTOR THAT BINDS THERETO

(75) Inventors: Raymond G. Goodwin; Craig A. Smith, both of Seattle; Mark R. Alderson, Bainbridge Island, all of WA (US)

(73) Assignee: Immunex Corporation, Seattle, WA (US)

( * ) Notice: Subject to any disclaimer, the term of this patent is extended or adjusted under 35 U.S.C. 154(b) by 0 days.

(21) Appl. No.: 09/150,864

(22) Filed: Sep. 10, 1998

Related U.S. Application Data

(60) Division of application No. 08/910,449, filed on Aug. 5, 1997, which is a division of application No. 08/236,918, filed on May 6, 1994, now Pat. No. 5,674,704, which is a continuation-in-part of application No. 08/060,843, filed on May 7, 1993, now abandoned.

(51) Int. Cl.[7] .......................... C07K 16/00; C07K 1/00; C12P 21/08; C12P 21/02; C12N 15/12
(52) U.S. Cl. ........................... 530/388.23; 530/388.22; 530/350; 530/351; 435/69.1; 436/501; 536/23.5; 536/24.31
(58) Field of Search .................. 530/388.23, 350, 530/351, 388.22; 436/501; 435/7.1, 7.2, 69.1, 252.3; 536/23.5, 24.31

(56) References Cited

U.S. PATENT DOCUMENTS

| | | | |
|---|---|---|---|
| 4,675,285 A | 6/1987 | Clark et al. | 435/6 |
| 5,030,576 A | 7/1991 | Dull et al. | 435/69 |
| 5,217,880 A | 6/1993 | Mitta et al. | 435/69.1 |
| 5,312,733 A | 5/1994 | MacLeod | 435/69.1 |

OTHER PUBLICATIONS

Kwon, B. and Weissman, S., "cDNA sequences of two inducible T-cell genes", *Proc. Natl. Acad. Sci. USA*, 86:1963–1967, Mar. 1989.

Kwon, B. et al., "Expression Characteristics of Two Potential T Cell Mediator Genes", *Cellular Immunology*, 121;414–422, 1989.

Kwon, B. et al., "Isolation and initial characterization of multiple species of T-lymphocyte subset cDNA clones," *Proc. Natl. Acad. Sc.USA*, 84:2896–2900, May 1987.

Pollok, K. et al., "Inducible T Cell Antigen 4–1BB", *The Journal of Immunology*, 150:771–781, Feb. 1, 1993.

Mallet, S. and Barclay, A.N., "A new superfamily of cell surface proteins related to the nerve growth factor receptor", *Immunology Today*, 12:220–223, 1991.

Schwartz et al., "cDNA Sequence Tissue Distribution and Regulation of Expression of a New Member of the Human TNF–NGF Receptor Family", *Arthritis Rheum.* 35 (9 Suppl.), Abstract D63, p. S224, 1992.

Schwartz et al., "Identification of a New Member of the Human Nerve Growth Factor/Tumor Necrosis Factor Receptor Family," *J. Immunology 150*: 298A, Abstract No. 1705, 1993.

Chalupny, N. et al., "T–cell activation molecule 4–1BB binds to extracellular matrix proteins", *Proc. Natl. Acad. Sci.USA*, 89:10360–64, Nov. 1992.

Flanagan, J. and Leder, P., "The kit Ligand: A Cell Surface Molecule Altered in Steel Mutant Fibroblasts", *Cell* 63:185–194, Oct. 5, 1990.

Aruffo, A. and Seed, B., "Molecular cloning of a CD28 cDNA by a high–efficiency COS cell expression system", *Proc. Natl. Acad. Sci. USA 84*: 8573–8577, Dec. 1987.

Capon, D., et al., "Designing CD4 immunoadhesins for AIDS therapy", *Nature 337*: 525–531, Feb. 9, 1989.

Steele, R.E., "Factor hunting made easier", *TIBS* 16:125–126, Apr. 1991.

Armitage, R., et al., "Molecular and biological characterization of a murine ligand for CD40", *Nature 357*: 80–82 (1992).

Hollenbaugh, D., et al., "The human T cell antigen gp39, a member of the TNF gene family, is a ligand for the CD40 receptor: expression of a soluble form of gp39 with B cell co–stimulatory activity", *The Embo Journal 11*: 4313–4321 (1992).

Ohtsuka, E., et al., "An Alternative Approach to Deoxyoligonucleotides as Hybridization Probes by Insertion of Neoxyinosine at Ambiguous Codon Positions," *Journal of Biol. Chemistry 260*: (5) 2605–2608, 1985.

Frohman, M., et al., "Rapid production of full–length cDNAs form rare transcripts: Amplification using a single gene–specific oligonucleotide primer," *Proc. Natl. Acad. Sci. USA*, 85:8998–9002, 1998.

Primary Examiner—Yvonne Eyler
Assistant Examiner—Michael Brannock
(74) Attorney, Agent, or Firm—Janis C. Henry; Simone L. Jones; James E. Klaniecki

(57) ABSTRACT

Novel 4-1BB ligand (4-1BB-L) polypeptides and a human cell surface receptor designated 4-1BB that binds 4-1BB-L are provided. Isolated 4-1BB-L-encoding and human 4-1BB-encoding DNA sequences, recombinant expression vectors comprising the isolated DNA sequences, and host cells transformed with the recombinant expression vectors are disclosed, along with methods for producing the novel polypeptides by cultivating such transformed host cells. Soluble forms of the 4-1BB-L or 4-1BB polypeptides are derived from the extracellular domains thereof.

4 Claims, 4 Drawing Sheets

SEQUENCE LISTING

<160> NUMBER OF SEQ ID NOS: 18

<210> SEQ ID NO 1
<211> LENGTH: 1254
<212> TYPE: DNA
<213> ORGANISM: Mus sp. (clone: murine 4-1BB-L)
<220> FEATURE:
<221> NAME/KEY: CDS
<222> LOCATION: (53)..(979)

<400> SEQUENCE: 1

```
agcctataaa gcacgggcac tggcgggaga cgtgcactga ccgaccgtgg ta atg gac      58
                                                         Met Asp
                                                           1 cag cac aca ctt gat gtg gag gat acc gcg gat gcc aga cat cca gca       106
Gln His Thr Leu Asp Val Glu Asp Thr Ala Asp Ala Arg His Pro Ala
              5                  10                  15 ggt act tcg tgc ccc tcg gat gcg gcg ctc ctc aga gat acc ggg ctc       154
Gly Thr Ser Cys Pro Ser Asp Ala Ala Leu Leu Arg Asp Thr Gly Leu
         20                  25                  30 ctc gcg gac gct gcg ctc ctc tca gat act gtg cgc ccc aca aat gcc       202
Leu Ala Asp Ala Ala Leu Leu Ser Asp Thr Val Arg Pro Thr Asn Ala
 35                  40                  45                  50 gcg ctc ccc acg gat gct gcc tac cct gcg gtt aat gtt cgg gat cgc       250
Ala Leu Pro Thr Asp Ala Ala Tyr Pro Ala Val Asn Val Arg Asp Arg
                 55                  60                  65 gag gcc gcg tgg ccg cct gca ctg aac ttc tgt tcc cgc cac cca aag       298
Glu Ala Ala Trp Pro Pro Ala Leu Asn Phe Cys Ser Arg His Pro Lys
             70                  75                  80 ctc tat ggc cta gtc gct ttg gtt ttg ctg ctt ctg atc gcc gcc tgt       346
Leu Tyr Gly Leu Val Ala Leu Val Leu Leu Leu Leu Ile Ala Ala Cys
         85                  90                  95 gtt cct atc ttc acc cgc acc gag cct cgg cca gcg ctc aca atc acc       394
Val Pro Ile Phe Thr Arg Thr Glu Pro Arg Pro Ala Leu Thr Ile Thr
    100                 105                 110 acc tcg ccc aac ctg ggt acc cga gag aat aat gca gac cag gtc acc       442
Thr Ser Pro Asn Leu Gly Thr Arg Glu Asn Asn Ala Asp Gln Val Thr
115                 120                 125                 130 cct gtt tcc cac att ggc tgc ccc aac act aca caa cag ggc tct cct       490
Pro Val Ser His Ile Gly Cys Pro Asn Thr Thr Gln Gln Gly Ser Pro
                135                 140                 145 gtg ttc gcc aag cta ctg gct aaa aac caa gca tcg ttg tgc aat aca       538
Val Phe Ala Lys Leu Leu Ala Lys Asn Gln Ala Ser Leu Cys Asn Thr
            150                 155                 160 act ctg aac tgg cac agc caa gat gga gct ggg agc tca tac cta tct       586
Thr Leu Asn Trp His Ser Gln Asp Gly Ala Gly Ser Ser Tyr Leu Ser
        165                 170                 175 caa ggt ctg agg tac gaa gaa gac aaa aag gag ttg gtg gta gac agt       634
Gln Gly Leu Arg Tyr Glu Glu Asp Lys Lys Glu Leu Val Val Asp Ser
    180                 185                 190 ccc ggg ctc tac tac gta ttt ttg gaa ctg aag ctc agt cca aca ttc       682
Pro Gly Leu Tyr Tyr Val Phe Leu Glu Leu Lys Leu Ser Pro Thr Phe
195                 200                 205                 210 aca aac aca ggc cac aag gtg cag ggc tgg gtc tct ctt gtt ttg caa       730
Thr Asn Thr Gly His Lys Val Gln Gly Trp Val Ser Leu Val Leu Gln
                215                 220                 225 gca aag cct cag gta gat gac ttt gac aac ttg gcc ctg aca gtg gaa       778
Ala Lys Pro Gln Val Asp Asp Phe Asp Asn Leu Ala Leu Thr Val Glu
            230                 235                 240
```

-continued

```
ctg ttc cct tgc tcc atg gag aac aag tta gtg gac cgt tcc tgg agt      826
Leu Phe Pro Cys Ser Met Glu Asn Lys Leu Val Asp Arg Ser Trp Ser
        245                 250                 255 caa ctg ttg ctc ctg aag gct ggc cac cgc ctc agt gtg ggt ctg agg      874
Gln Leu Leu Leu Leu Lys Ala Gly His Arg Leu Ser Val Gly Leu Arg
    260                 265                 270 gct tat ctg cat gga gcc cag gat gca tac aga gac tgg gag ctg tct      922
Ala Tyr Leu His Gly Ala Gln Asp Ala Tyr Arg Asp Trp Glu Leu Ser
275                 280                 285                 290 tat ccc aac acc acc agc ttt gga ctc ttt ctt gtg aaa ccc gac aac      970
Tyr Pro Asn Thr Thr Ser Phe Gly Leu Phe Leu Val Lys Pro Asp Asn
                295                 300                 305 cca tgg gaa tgagaactat ccttcttgtg actcctagtt gctaagtcct             1019
Pro Trp Glu caagctgcta tgttttatgg ggtctgagca ggggtccctt ccatgacttt ctcttgtctt    1079
taactggact tggtatttat tctgagcata gctcagacaa gactttatat aattcactag    1139
atagcattag taaactgctg gcagctgct agataaaaaa aaatttctaa atcaaagttt    1199
atatttatat taatatataa aaataaatgt gtttgtaaat aaaaaaaaaa aaaaa        1254
```

<210> SEQ ID NO 2
<211> LENGTH: 309
<212> TYPE: PRT
<213> ORGANISM: Mus sp. (clone: murine 4-1BB-L)

<400> SEQUENCE: 2

```
Met Asp Gln His Thr Leu Asp Val Glu Asp Thr Ala Asp Ala Arg His
 1               5                  10                  15

Pro Ala Gly Thr Ser Cys Pro Ser Asp Ala Ala Leu Leu Arg Asp Thr
            20                  25                  30

Gly Leu Leu Ala Asp Ala Ala Leu Leu Ser Asp Thr Val Arg Pro Thr
        35                  40                  45

Asn Ala Ala Leu Pro Thr Asp Ala Ala Tyr Pro Ala Val Asn Val Arg
    50                  55                  60

Asp Arg Glu Ala Ala Trp Pro Pro Ala Leu Asn Phe Cys Ser Arg His
65                  70                  75                  80

Pro Lys Leu Tyr Gly Leu Val Ala Leu Val Leu Leu Leu Ile Ala
                85                  90                  95

Ala Cys Val Pro Ile Phe Thr Arg Thr Glu Pro Arg Pro Ala Leu Thr
            100                 105                 110

Ile Thr Thr Ser Pro Asn Leu Gly Thr Arg Glu Asn Asn Ala Asp Gln
        115                 120                 125

Val Thr Pro Val Ser His Ile Gly Cys Pro Asn Thr Thr Gln Gln Gly
    130                 135                 140

Ser Pro Val Phe Ala Lys Leu Leu Ala Lys Asn Gln Ala Ser Leu Cys
145                 150                 155                 160

Asn Thr Thr Leu Asn Trp His Ser Gln Asp Gly Ala Gly Ser Ser Tyr
                165                 170                 175

Leu Ser Gln Gly Leu Arg Tyr Glu Glu Asp Lys Lys Glu Leu Val Val
            180                 185                 190

Asp Ser Pro Gly Leu Tyr Tyr Val Phe Leu Glu Leu Lys Leu Ser Pro
        195                 200                 205

Thr Phe Thr Asn Thr Gly His Lys Val Gln Gly Trp Val Ser Leu Val
    210                 215                 220

Leu Gln Ala Lys Pro Gln Val Asp Asp Phe Asp Asn Leu Ala Leu Thr
225                 230                 235                 240
```

```
Val Glu Leu Phe Pro Cys Ser Met Glu Asn Lys Leu Val Asp Arg Ser
                245                 250                 255

Trp Ser Gln Leu Leu Leu Lys Ala Gly His Arg Leu Ser Val Gly
        260                 265                 270

Leu Arg Ala Tyr Leu His Gly Ala Gln Asp Ala Tyr Arg Asp Trp Glu
            275                 280                 285

Leu Ser Tyr Pro Asn Thr Thr Ser Phe Gly Leu Phe Leu Val Lys Pro
        290                 295                 300

Asp Asn Pro Trp Glu
305

<210> SEQ ID NO 3
<211> LENGTH: 1618
<212> TYPE: DNA
<213> ORGANISM: Homo sapiens(clone: human4-1BB-L(7A)
<220> FEATURE:
<221> NAME/KEY: CDS
<222> LOCATION: (4)..(765)

<400> SEQUENCE: 3 gtc atg gaa tac gcc tct gac gct tca ctg gac ccc gaa gcc ccg tgg        48
    Met Glu Tyr Ala Ser Asp Ala Ser Leu Asp Pro Glu Ala Pro Trp
    1               5                  10                  15 cct ccc gcg ccc cgc gct cgc gcc tgc cgc gta ctg cct tgg gcc ctg        96
Pro Pro Ala Pro Arg Ala Arg Ala Cys Arg Val Leu Pro Trp Ala Leu
                20                  25                  30 gtc gcg ggg ctg ctg ctg ctg ctg ctc gct gcc gcc tgc gcc gtc           144
Val Ala Gly Leu Leu Leu Leu Leu Leu Ala Ala Ala Cys Ala Val
            35                  40                  45 ttc ctc gcc tgc ccc tgg gcc gtg tcc ggg gct cgc gcc tcg ccc ggc       192
Phe Leu Ala Cys Pro Trp Ala Val Ser Gly Ala Arg Ala Ser Pro Gly
        50                  55                  60 tcc gcg gcc agc ccg aga ctc cgc gag ggt ccc gag ctt tcg ccc gac       240
Ser Ala Ala Ser Pro Arg Leu Arg Glu Gly Pro Glu Leu Ser Pro Asp
65                  70                  75 gat ccc gcc ggc ctc ttg gac ctg cgg cag ggc atg ttt gcg cag ctg       288
Asp Pro Ala Gly Leu Leu Asp Leu Arg Gln Gly Met Phe Ala Gln Leu
 80                  85                  90                  95 gtg gcc caa aat gtt ctg ctg atc gat ggg ccc ctg agc tgg tac agt       336
Val Ala Gln Asn Val Leu Leu Ile Asp Gly Pro Leu Ser Trp Tyr Ser
                100                 105                 110 gac cca ggc ctg gca ggc gtg tcc ctg acg ggg ggc ctg agc tac aaa       384
Asp Pro Gly Leu Ala Gly Val Ser Leu Thr Gly Gly Leu Ser Tyr Lys
            115                 120                 125 gag gac acg aag gag ctg gtg gtg gcc aag gct gga gtc tac tat gtc       432
Glu Asp Thr Lys Glu Leu Val Val Ala Lys Ala Gly Val Tyr Tyr Val
        130                 135                 140 ttc ttt caa cta gag ctg cgg cgc gtg gtg gcc ggc gag ggc tca ggc       480
Phe Phe Gln Leu Glu Leu Arg Arg Val Val Ala Gly Glu Gly Ser Gly
    145                 150                 155 tcc gtt tca ctt gcg ctg cac ctg cag cca ctg cgc tct gct gct ggg       528
Ser Val Ser Leu Ala Leu His Leu Gln Pro Leu Arg Ser Ala Ala Gly
160                 165                 170                 175 gcc gcc gcc ctg gct ttg acc gtg gac ctg cca ccc gcc tcc tcc gag       576
Ala Ala Ala Leu Ala Leu Thr Val Asp Leu Pro Pro Ala Ser Ser Glu
                180                 185                 190 gct cgg aac tcg gcc ttc ggt ttc cag ggc cgc ttg ctg cac ctg agt       624
Ala Arg Asn Ser Ala Phe Gly Phe Gln Gly Arg Leu Leu His Leu Ser
            195                 200                 205
```

-continued

| | | | | | | | | | | | | |
|---|---|---|---|---|---|---|---|---|---|---|---|---|
| gcc | ggc | cag | cgc | ctg | ggc | gtc | cat | ctt | cac | act | gag | gcc | agg | gca | cgc | 672 |
| Ala | Gly | Gln | Arg | Leu | Gly | Val | His | Leu | His | Thr | Glu | Ala | Arg | Ala | Arg | |
| | 210 | | | | | 215 | | | | | 220 | | | | | |

```
gcc ggc cag cgc ctg ggc gtc cat ctt cac act gag gcc agg gca cgc      672
Ala Gly Gln Arg Leu Gly Val His Leu His Thr Glu Ala Arg Ala Arg
        210                 215                 220 cat gcc tgg cag ctt acc cag ggc gcc aca gtc ttg gga ctc ttc cgg      720
His Ala Trp Gln Leu Thr Gln Gly Ala Thr Val Leu Gly Leu Phe Arg
    225                 230                 235 gtg acc ccc gaa atc cca gcc gga ctc cct tca ccg agg tcg gaa          765
Val Thr Pro Glu Ile Pro Ala Gly Leu Pro Ser Pro Arg Ser Glu
240                 245                 250 aacgcccagc ctgggtgcag cccacctgga cagagtccga atcctactcc atccttcatg    825
gagacccctg gtgctgggtc cctgctgctt tctctacctc aaggggcttg gcagggggtcc   885
ctgctgctga cctccccttg aggacccctcc tcacccactc cttccccaag ttggaccttg   945
atatttattc tgagcctgag ctcagataat atattatata tattatatat atatatatat  1005
ttctatttaa agaggatcct gagtttgtga atggactttt ttagaggagt tgttttgggg  1065
gggggggtctt cgacattgcc gaggctggtc ttgaactcct ggacttagac gatcctcctg  1125
cctcagcctc ccaagcaact gggattcatc ctttctatta attcattgta cttatttgcc  1185
tatttgtgtg tattgagcat ctgtaatgtg ccagcattgt gcccaggcta ggggggctata  1245
gaaacatcta gaaatagact gaaagaaaat ctgagttatg gtaatacgtg aggaattttaa  1305
agactcatcc ccagcctcca cctcctgtgt gatacttggg ggctagcttt tttctttctt   1365
tctttttttt gagatggtct tgttctgtca accaggctag aatgcagcgg tgcaatcatg   1425
agtcaatgca gcctccagcc tcgacctccc gaggctcagg tgatcctccc atctcagcct   1485
ctcgagtagc tgggaccaca gttgtgtgcc accacacttg gctaactttt taatttttttt  1545
gcggagacgg tattgctatg ttgccaaggt tgtttacatg ccagtacaat ttataataaa   1605
cactcatttt tcc                                                     1618
```

<210> SEQ ID NO 4
<211> LENGTH: 254
<212> TYPE: PRT
<213> ORGANISM: Homo sapiens(clone: human4-1BB-L(7A)

<400> SEQUENCE: 4

```
Met Glu Tyr Ala Ser Asp Ala Ser Leu Asp Pro Glu Ala Pro Trp Pro
  1               5                  10                  15

Pro Ala Pro Arg Ala Arg Ala Cys Arg Val Leu Pro Trp Ala Leu Val
                 20                  25                  30

Ala Gly Leu Leu Leu Leu Leu Leu Ala Ala Ala Cys Ala Val Phe
             35                  40                  45

Leu Ala Cys Pro Trp Ala Val Ser Gly Ala Arg Ala Ser Pro Gly Ser
     50                  55                  60

Ala Ala Ser Pro Arg Leu Arg Glu Gly Pro Glu Leu Ser Pro Asp Asp
 65                  70                  75                  80

Pro Ala Gly Leu Leu Asp Leu Arg Gln Gly Met Phe Ala Gln Leu Val
                 85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125

Asp Thr Lys Glu Leu Val Val Ala Lys Ala Gly Val Tyr Tyr Val Phe
    130                 135                 140

Phe Gln Leu Glu Leu Arg Arg Val Val Ala Gly Glu Gly Ser Gly Ser
145                 150                 155                 160
```

```
Val Ser Leu Ala Leu His Leu Gln Pro Leu Arg Ser Ala Ala Gly Ala
            165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
            195                 200                 205

Gly Gln Arg Leu Gly Val His Leu His Thr Glu Ala Arg Ala Arg His
            210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                    245                 250

<210> SEQ ID NO 5
<211> LENGTH: 768
<212> TYPE: DNA
<213> ORGANISM: Mus sp. (clone: mu4-1BB)
<220> FEATURE:
<221> NAME/KEY: CDS
<222> LOCATION: (1)..(768)
<221> NAME/KEY: mat_peptide
<222> LOCATION: (70)..(768)
<221> NAME/KEY: sig_peptide
<222> LOCATION: (1)..(69)

<400> SEQUENCE: 5 atg gga aac aac tgt tac aac gtg gtg gtc att gtg ctg ctg cta gtg      48
Met Gly Asn Asn Cys Tyr Asn Val Val Val Ile Val Leu Leu Leu Val
            -20                 -15                 -10 ggc tgt gag aag gtg gga gcc gtg cag aac tcc tgt gat aac tgt cag      96
Gly Cys Glu Lys Val Gly Ala Val Gln Asn Ser Cys Asp Asn Cys Gln
        -5                  -1   1               5 cct ggt act ttc tgc aga aaa tac aat cca gtc tgc aag agc tgc cct     144
Pro Gly Thr Phe Cys Arg Lys Tyr Asn Pro Val Cys Lys Ser Cys Pro
 10                  15                  20                  25 cca agt acc ttc tcc agc ata ggt gga cag ccg aac tgt aac atc tgc     192
Pro Ser Thr Phe Ser Ser Ile Gly Gly Gln Pro Asn Cys Asn Ile Cys
                 30                  35                  40 aga gtg tgt gca ggc tat ttc agg ttc aag aag ttt tgc tcc tct acc     240
Arg Val Cys Ala Gly Tyr Phe Arg Phe Lys Lys Phe Cys Ser Ser Thr
             45                  50                  55 cac aac gcg gag tgt gag tgc att gaa gga ttc cat tgc ttg ggg cca     288
His Asn Ala Glu Cys Glu Cys Ile Glu Gly Phe His Cys Leu Gly Pro
 60                  65                  70 cag tgc acc aga tgt gaa aag gac tgc agg cct ggc cag gag cta acg     336
Gln Cys Thr Arg Cys Glu Lys Asp Cys Arg Pro Gly Gln Glu Leu Thr
     75                  80                  85 aag cag ggt tgc aaa acc tgt agc ttg gga aca ttt aat gac cag aac     384
Lys Gln Gly Cys Lys Thr Cys Ser Leu Gly Thr Phe Asn Asp Gln Asn
 90                  95                 100                 105 ggt act ggc gtc tgt cga ccc tgg acg aac tgc tct cta gac gga agg     432
Gly Thr Gly Val Cys Arg Pro Trp Thr Asn Cys Ser Leu Asp Gly Arg
             110                 115                 120 tct gtg ctt aag acc ggg acc acg gag aag gac gtg gtg tgt gga ccc     480
Ser Val Leu Lys Thr Gly Thr Thr Glu Lys Asp Val Val Cys Gly Pro
 125                 130                 135 cct gtg gtg agc ttc tct ccc agt acc acc att tct gtg act cca gag     528
Pro Val Val Ser Phe Ser Pro Ser Thr Thr Ile Ser Val Thr Pro Glu
             140                 145                 150
```

```
gga gga cca gga ggg cac tcc ttg cag gtc ctt acc ttg ttc ctg gcg    576
Gly Gly Pro Gly Gly His Ser Leu Gln Val Leu Thr Leu Phe Leu Ala
    155                 160                 165 ctg aca tcg gct ttg ctg ctg gcc ctg atc ttc att act ctc ctg ttc    624
Leu Thr Ser Ala Leu Leu Leu Ala Leu Ile Phe Ile Thr Leu Leu Phe
170                 175                 180                 185 tct gtg ctc aaa tgg atc agg aaa aaa ttc ccc cac ata ttc aag caa    672
Ser Val Leu Lys Trp Ile Arg Lys Lys Phe Pro His Ile Phe Lys Gln
                190                 195                 200 cca ttt aag aag acc act gga gca gct caa gag gaa gat gct tgt agc    720
Pro Phe Lys Lys Thr Thr Gly Ala Ala Gln Glu Glu Asp Ala Cys Ser
                205                 210                 215 tgc cga tgt cca cag gaa gaa gaa gga gga gga gga ggc tat gag ctg    768
Cys Arg Cys Pro Gln Glu Glu Glu Gly Gly Gly Gly Gly Tyr Glu Leu
        220                 225                 230
```

<210> SEQ ID NO 6
<211> LENGTH: 256
<212> TYPE: PRT
<213> ORGANISM: Mus sp. (clone: mu4-1BB)

<400> SEQUENCE: 6

```
Met Gly Asn Asn Cys Tyr Asn Val Val Ile Val Leu Leu Leu Val
        -20                 -15                 -10

Gly Cys Glu Lys Val Gly Ala Val Gln Asn Ser Cys Asp Asn Cys Gln
         -5              -1   1               5

Pro Gly Thr Phe Cys Arg Lys Tyr Asn Pro Val Cys Lys Ser Cys Pro
 10                  15                  20                  25

Pro Ser Thr Phe Ser Ser Ile Gly Gly Gln Pro Asn Cys Asn Ile Cys
                 30                  35                  40

Arg Val Cys Ala Gly Tyr Phe Arg Phe Lys Lys Phe Cys Ser Ser Thr
                 45                  50                  55

His Asn Ala Glu Cys Glu Cys Ile Glu Gly Phe His Cys Leu Gly Pro
             60                  65                  70

Gln Cys Thr Arg Cys Glu Lys Asp Cys Arg Pro Gly Gln Glu Leu Thr
 75                  80                  85

Lys Gln Gly Cys Lys Thr Cys Ser Leu Gly Thr Phe Asn Asp Gln Asn
 90                  95                  100                 105

Gly Thr Gly Val Cys Arg Pro Trp Thr Asn Cys Ser Leu Asp Gly Arg
                 110                 115                 120

Ser Val Leu Lys Thr Gly Thr Thr Glu Lys Asp Val Val Cys Gly Pro
                 125                 130                 135

Pro Val Val Ser Phe Ser Pro Ser Thr Thr Ile Ser Val Thr Pro Glu
             140                 145                 150

Gly Gly Pro Gly Gly His Ser Leu Gln Val Leu Thr Leu Phe Leu Ala
    155                 160                 165

Leu Thr Ser Ala Leu Leu Leu Ala Leu Ile Phe Ile Thr Leu Leu Phe
170                 175                 180                 185

Ser Val Leu Lys Trp Ile Arg Lys Lys Phe Pro His Ile Phe Lys Gln
                190                 195                 200

Pro Phe Lys Lys Thr Thr Gly Ala Ala Gln Glu Glu Asp Ala Cys Ser
                205                 210                 215

Cys Arg Cys Pro Gln Glu Glu Glu Gly Gly Gly Gly Gly Tyr Glu Leu
        220                 225                 230
```

```
<210> SEQ ID NO 7
<211> LENGTH: 1415
<212> TYPE: DNA
<213> ORGANISM: Homo sapiens (clone: hu4-1BB)
<220> FEATURE:
<221> NAME/KEY: mat_peptide
<222> LOCATION: (189)..(884)
<221> NAME/KEY: sig_peptide
<222> LOCATION: (120)..(188)
<221> NAME/KEY: CDS
<222> LOCATION: (120)..(884)

<400> SEQUENCE: 7
agtggaaagt tctccggcag ccctgagatc tcaagagtga catttgtgag accagctaat      60
ttgattaaaa ttctcttgga atcagctttg ctagtatcat acctgtgcca gatttcatc     119 atg gga aac agc tgt tac aac ata gta gcc act ctg ttg ctg gtc ctc      167
Met Gly Asn Ser Cys Tyr Asn Ile Val Ala Thr Leu Leu Leu Val Leu
        -20             -15                 -10 aac ttt gag agg aca aga tca ttg cag gat cct tgt agt aac tgc cca      215
Asn Phe Glu Arg Thr Arg Ser Leu Gln Asp Pro Cys Ser Asn Cys Pro
     -5              -1   1               5 gct ggt aca ttc tgt gat aat aac agg aat cag att tgc agt ccc tgt      263
Ala Gly Thr Phe Cys Asp Asn Asn Arg Asn Gln Ile Cys Ser Pro Cys
 10              15                  20                  25 cct cca aat agt ttc tcc agc gca ggt gga caa agg acc tgt gac ata      311
Pro Pro Asn Ser Phe Ser Ser Ala Gly Gly Gln Arg Thr Cys Asp Ile
             30                  35                  40 tgc agg cag tgt aaa ggt gtt ttc agg acc agg aag gag tgt tcc tcc      359
Cys Arg Gln Cys Lys Gly Val Phe Arg Thr Arg Lys Glu Cys Ser Ser
         45                  50                  55 acc agc aat gca gag tgt gac tgc act cca ggg ttt cac tgc ctg ggg      407
Thr Ser Asn Ala Glu Cys Asp Cys Thr Pro Gly Phe His Cys Leu Gly
     60                  65                  70 gca gga tgc agc atg tgt gaa cag gat tgt aaa caa ggt caa gaa ctg      455
Ala Gly Cys Ser Met Cys Glu Gln Asp Cys Lys Gln Gly Gln Glu Leu
 75                  80                  85 aca aaa aaa ggt tgt aaa gac tgt tgc ttt ggg aca ttt aac gat cag      503
Thr Lys Lys Gly Cys Lys Asp Cys Cys Phe Gly Thr Phe Asn Asp Gln
 90                  95                  100                 105 aaa cgt ggc atc tgt cga ccc tgg aca aac tgt tct ttg gat gga aag      551
Lys Arg Gly Ile Cys Arg Pro Trp Thr Asn Cys Ser Leu Asp Gly Lys
             110                 115                 120 tct gtg ctt gtg aat ggg acg aag gag agg gac gtg gtc tgt gga cca      599
Ser Val Leu Val Asn Gly Thr Lys Glu Arg Asp Val Val Cys Gly Pro
         125                 130                 135 tct cca gcc gac ctc tct ccg gga gca tcc tct gtg acc ccg cct gcc      647
Ser Pro Ala Asp Leu Ser Pro Gly Ala Ser Ser Val Thr Pro Pro Ala
     140                 145                 150 cct gcg aga gag cca gga cac tct ccg cag atc atc tcc ttc ttt ctt      695
Pro Ala Arg Glu Pro Gly His Ser Pro Gln Ile Ile Ser Phe Phe Leu
 155                 160                 165 gcg ctg acg tcg act gcg ttg ctc ttc ctg ctg ttc ctc acg ctc          743
Ala Leu Thr Ser Thr Ala Leu Leu Phe Leu Leu Phe Phe Leu Thr Leu
 170                 175                 180                 185 cgt ttc tct gtt gtt aaa cgg ggc aga aag aaa ctc ctg tat ata ttc      791
Arg Phe Ser Val Val Lys Arg Gly Arg Lys Lys Leu Leu Tyr Ile Phe
             190                 195                 200 aaa caa cca ttt atg aga cca gta caa act act caa gag gaa gat ggc      839
Lys Gln Pro Phe Met Arg Pro Val Gln Thr Thr Gln Glu Glu Asp Gly
         205                 210                 215
```

-continued

```
tgt agc tgc cga ttt cca gaa gaa gaa gaa gga gga tgt gaa ctg        884
Cys Ser Cys Arg Phe Pro Glu Glu Glu Glu Gly Gly Cys Glu Leu
            220                 225                 230 tgaaatggaa gtcaataggg ctgttgggac tttcttgaaa agaagcaagg aaatatgagt  944
catccgctat cacagctttc aaaagcaaga acaccatcct acataatacc caggattccc 1004 ccaacacacg ttcttttcta aatgccaatg agttggcctt taaaaatgca ccactttttt 1064 ttttttttt gacagggtct cactctgtca cccaggctgg agtgcagtgg caccaccatg  1124
gctctctgca gccttgacct ctgggagctc aagtgatcct cctgcctcag tctcctagta 1184 gctggaacta caaggaaggg ccaccacacc tgactaactt ttttgttttt tgtttggtaa 1244 agatggcatt tcgccatgtt gtacaggctg gtctcaaact cctaggttca ctttggcctc 1304 ccaaagtgct gggattacag acatgaactg ccaggcccgg ccaaaataat gcaccacttt 1364 taacagaaca gacagatgag gacagagctg gtgataaaaa aaaaaaaaaa a          1415
```

<210> SEQ ID NO 8
<211> LENGTH: 255
<212> TYPE: PRT
<213> ORGANISM: Homo sapiens (clone: hu4-1BB)

<400> SEQUENCE: 8

```
Met Gly Asn Ser Cys Tyr Asn Ile Val Ala Thr Leu Leu Leu Val Leu
            -20                 -15                 -10

Asn Phe Glu Arg Thr Arg Ser Leu Gln Asp Pro Cys Ser Asn Cys Pro
        -5                  -1   1               5

Ala Gly Thr Phe Cys Asp Asn Asn Arg Asn Gln Ile Cys Ser Pro Cys
 10                  15                  20                  25

Pro Pro Asn Ser Phe Ser Ser Ala Gly Gly Gln Arg Thr Cys Asp Ile
                30                  35                  40

Cys Arg Gln Cys Lys Gly Val Phe Arg Thr Arg Lys Glu Cys Ser Ser
            45                  50                  55

Thr Ser Asn Ala Glu Cys Asp Cys Thr Pro Gly Phe His Cys Leu Gly
        60                  65                  70

Ala Gly Cys Ser Met Cys Glu Gln Asp Cys Lys Gln Gly Gln Glu Leu
    75                  80                  85

Thr Lys Lys Gly Cys Lys Asp Cys Cys Phe Gly Thr Phe Asn Asp Gln
 90                  95                 100                 105

Lys Arg Gly Ile Cys Arg Pro Trp Thr Asn Cys Ser Leu Asp Gly Lys
                110                 115                 120

Ser Val Leu Val Asn Gly Thr Lys Glu Arg Asp Val Val Cys Gly Pro
            125                 130                 135

Ser Pro Ala Asp Leu Ser Pro Gly Ala Ser Ser Val Thr Pro Pro Ala
        140                 145                 150

Pro Ala Arg Glu Pro Gly His Ser Pro Gln Ile Ile Ser Phe Phe Leu
    155                 160                 165

Ala Leu Thr Ser Thr Ala Leu Leu Phe Leu Leu Phe Phe Leu Thr Leu
170                 175                 180                 185

Arg Phe Ser Val Val Lys Arg Gly Arg Lys Lys Leu Leu Tyr Ile Phe
                190                 195                 200

Lys Gln Pro Phe Met Arg Pro Val Gln Thr Thr Gln Glu Glu Asp Gly
            205                 210                 215

Cys Ser Cys Arg Phe Pro Glu Glu Glu Glu Gly Gly Cys Glu Leu
        220                 225                 230
```

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 9
gtcactagtt ctgtgcagaa ctcctgtgat aac                           33

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 10
cacaagatct gggctcctct ggagtcacag aaatg                         35

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 11
cagactagtt cactctggag tcacagaaat g                             31

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 12
atagcggccg ctgccagatt tcatcatggg aaac                          34

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 13
acaagatctg ggctcctgcg gagagtgtcc tggctctctc                    40

<210> SEQ ID NO 14
<211> LENGTH: 745
<212> TYPE: DNA
<213> ORGANISM: Homo sapiens (clone: hIgG1Fc)
<220> FEATURE:
<221> NAME/KEY: CDS
<222> LOCATION: (2)..(739)

<400> SEQUENCE: 14

```
g gta ccg cta gcg tcg aca ggc cta gga tat cga tac gta gag ccc aga    49
  Val Pro Leu Ala Ser Thr Gly Leu Gly Tyr Arg Tyr Val Glu Pro Arg
   1               5                  10                  15
```

```
tct tgt gac aaa act cac aca tgc cca ccg tgc cca gca cct gaa ctc    97
Ser Cys Asp Lys Thr His Thr Cys Pro Pro Cys Pro Ala Pro Glu Leu
            20                  25                  30 ctg ggg gga ccg tca gtc ttc ctc ttc ccc cca aaa ccc aag gac acc   145
Leu Gly Gly Pro Ser Val Phe Leu Phe Pro Pro Lys Pro Lys Asp Thr
        35                  40                  45 ctc atg atc tcc cgg acc cct gag gtc aca tgc gtg gtg gtg gac gtg   193
Leu Met Ile Ser Arg Thr Pro Glu Val Thr Cys Val Val Val Asp Val
    50                  55                  60 agc cac gaa gac cct gag gtc aag ttc aac tgg tac gtg gac ggc gtg   241
Ser His Glu Asp Pro Glu Val Lys Phe Asn Trp Tyr Val Asp Gly Val
65                  70                  75                  80 gag gtg cat aat gcc aag aca aag ccg cgg gag gag cag tac aac agc   289
Glu Val His Asn Ala Lys Thr Lys Pro Arg Glu Glu Gln Tyr Asn Ser
                85                  90                  95 acg tac cgg gtg gtc agc gtc ctc acc gtc ctg cac cag gac tgg ctg   337
Thr Tyr Arg Val Val Ser Val Leu Thr Val Leu His Gln Asp Trp Leu
            100                 105                 110 aat ggc aag gac tac aag tgc aag gtc tcc aac aaa gcc ctc cca gcc   385
Asn Gly Lys Asp Tyr Lys Cys Lys Val Ser Asn Lys Ala Leu Pro Ala
        115                 120                 125 ccc atg cag aaa acc atc tcc aaa gcc aaa ggg cag ccc cga gaa cca   433
Pro Met Gln Lys Thr Ile Ser Lys Ala Lys Gly Gln Pro Arg Glu Pro
    130                 135                 140 cag gtg tac acc ctg ccc cca tcc cgg gat gag ctg acc aag aac cag   481
Gln Val Tyr Thr Leu Pro Pro Ser Arg Asp Glu Leu Thr Lys Asn Gln
145                 150                 155                 160 gtc agc ctg acc tgc ctg gtc aaa ggc ttc tat ccc agg cac atc gcc   529
Val Ser Leu Thr Cys Leu Val Lys Gly Phe Tyr Pro Arg His Ile Ala
                165                 170                 175 gtg gag tgg gag agc aat ggg cag ccg gag aac aac tac aag acc acg   577
Val Glu Trp Glu Ser Asn Gly Gln Pro Glu Asn Asn Tyr Lys Thr Thr
            180                 185                 190 cct ccc gtg ctg gac tcc gac ggc tcc ttc ttc ctc tac agc aag ctc   625
Pro Pro Val Leu Asp Ser Asp Gly Ser Phe Phe Leu Tyr Ser Lys Leu
        195                 200                 205 acc gtg gac aag agc agg tgg cag cag ggg aac gtc ttc tca tgc tcc   673
Thr Val Asp Lys Ser Arg Trp Gln Gln Gly Asn Val Phe Ser Cys Ser
    210                 215                 220 gtg atg cat gag gct ctg cac aac cac tac acg cag aag agc ctc tcc   721
Val Met His Glu Ala Leu His Asn His Tyr Thr Gln Lys Ser Leu Ser
225                 230                 235                 240 ctg tct ccg ggt aaa tga actagt                                    745
Leu Ser Pro Gly Lys
                245
```

<210> SEQ ID NO 15
<211> LENGTH: 245
<212> TYPE: PRT
<213> ORGANISM: Homo sapiens (clone: hIgG1Fc)

<400> SEQUENCE: 15

```
Val Pro Leu Ala Ser Thr Gly Leu Gly Tyr Arg Tyr Val Glu Pro Arg
 1               5                  10                  15

Ser Cys Asp Lys Thr His Thr Cys Pro Pro Cys Pro Ala Pro Glu Leu
            20                  25                  30

Leu Gly Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60
```

```
Ser His Glu Asp Pro Glu Val Lys Phe Asn Trp Tyr Val Asp Gly Val
 65                  70                  75                  80

Glu Val His Asn Ala Lys Thr Lys Pro Arg Glu Glu Gln Tyr Asn Ser
             85                  90                  95

Thr Tyr Arg Val Val Ser Val Leu Thr Val Leu His Gln Asp Trp Leu
            100                 105                 110

Asn Gly Lys Asp Tyr Lys Cys Lys Val Ser Asn Lys Ala Leu Pro Ala
        115                 120                 125

Pro Met Gln Lys Thr Ile Ser Lys Ala Lys Gly Gln Pro Arg Glu Pro
130                 135                 140

Gln Val Tyr Thr Leu Pro Pro Ser Arg Asp Glu Leu Thr Lys Asn Gln
145                 150                 155                 160

Val Ser Leu Thr Cys Leu Val Lys Gly Phe Tyr Pro Arg His Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Lys Leu
        195                 200                 205

Thr Val Asp Lys Ser Arg Trp Gln Gln Gly Asn Val Phe Ser Cys Ser
210                 215                 220

Val Met His Glu Ala Leu His Asn His Tyr Thr Gln Lys Ser Leu Ser
225                 230                 235                 240

Leu Ser Pro Gly Lys
                245

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: FLAG
      peptide

<400> SEQUENCE: 16

Asp Tyr Lys Asp Asp Asp Asp Lys
 1               5

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence:
      peptide linker

<400> SEQUENCE: 17

Gly Gly Gly Gly Ser Gly Gly Gly Gly Ser
 1               5                  10

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence:
      peptide linker

<400> SEQUENCE: 18

Gly Gly Gly Gly Ser
 1               5
```

US 6,355,779 B1

CYTOKINE DESIGNATED 4-1BB LIGAND ANTIBODIES AND HUMAN RECEPTOR THAT BINDS THERETO

CROSS-REFERENCE TO RELATED APPLICATIONS

This application is a divisional of currently U.S. application Ser. No. 08/910,449 filed Aug. 5, 1997, which is a divisional of U.S. application Ser. No. 08/236,918, filed May 6, 1994 now U.S. Pat. No. 5,674,704, which is a continuation-in-part of U.S. application Ser. No. 8/060,843, filed May 7, 1993, abandoned.

BACKGROUND OF THE INVENTION

The term "cytokines" encompasses a diverse group of soluble proteins that are released by one type of cell and mediate a biological effect on another cell type. Biological activities exhibited by cytokines include control of proliferation, growth, and differentiation of various cell types, among which are cells of the hematopoietic or immune systems.

Examples of cytokines include the interleukins (e.g., interleukins 1 through 12), the interferons (IFNα, IFNβ, and IFNα), tumor necrosis factor (TNFα and TNFβ), epidermal growth factor (EGF), platelet-derived growth factor (PDGF), and colony stimulating factors. Examples of colony stimulating factors (CSF), which control growth and differentiation of hematopoietic cells, are granulocyte-CSF (G-CSF), granulocyte-macrophage-CSF (GM-CSF), macrophage-CSF (M-CSF or CSF-1), mast cell growth factor (MGF), and erythropoietin (EPO).

The biological activity of cytokines generally is mediated by binding of the cytokine to a receptor specific for that cytokine, located on the surface of target cells. Much research has been directed to identifying receptor(s) that bind a given cytokine (often referred to as the "ligand" for the receptor in question), and exploring the roles that endogenous ligands and receptors play in vivo.

One family of cytokine receptors includes two different TNF receptors (Type I and Type II) (Smith et al., *Science* 248:1019, 1990) and Schall et al., *Cell* 61:361, 1990); nerve growth factor receptor (Johnson et al., *Cell* 47:545, 1986); B cell antigen CD40 (Stamenkovic et al., *EMBO J.* 8:1403, 1989); T cell antigen OX40 (Mallett et al., *EMBO J.* 9:1063, 1990); human Fas antigen (Itoh et al., *Cell* 66:233, 1991); and murine receptor 4-1BB (Kwon et al., *Cell. Immunol.* 121:414, 1989) [Kwon et al. I] and Kwon et al., *Proc. Natl. Acad. Sci. USA* 86:1963, 1989 [Kwon et al. II]).

Expression of murine 4-1BB is induced by concanavalin A (con A) in spleen cells, cloned helper T cells, cytolytic T cells, and cytolytic T cell hybridomas (Kwon et al. II). Murine 4-1BB cDNA was isolated from a cDNA library made from induced RNA isolated from both a helper T cell line and a cytotoxic T cell line (Kwon et al. II). The nucleotide sequence of the isolated cDNA is presented in Kwon et al. II, along with the amino acid sequence encoded thereby. The murine 4-1BB protein comprises 256 amino acids, including a putative leader sequence, trans-membrane domain and a number of other features common to cell membrane bound receptor proteins. Regarding a putative human 4-1BB protein, neither amino acid nor nucleotide sequence information is known for any such protein.

No ligand that would bind 4-1BB and transduce a signal through the 4-1BB receptor is known. Thus, there is a need in the art to determine whether a novel protein functioning as a ligand for 4-1BB exists, and, if so, to isolate and characterize the 4-1BB ligand protein.

SUMMARY OF THE INVENTION

A novel cytokine designated 4-1BB ligand (4-1BB-L) is disclosed herein. 4-1BB-L polypeptides bind to the cell surface receptor designated 4-1BB. Human 4-1BB is also provided by the present invention.

The present invention provides purified 4-1BB-L polypeptides, exemplified by the murine and human 4-1BB-L proteins disclosed herein, and purified human 4-1BB polypeptides. Isolated DNA sequences encoding 4-1BB-L or human 4-1BB, recombinant expression vectors comprising the isolated DNA, and host cells transformed with the expression vectors are provided by the present invention, along with methods for producing 4-1BB-L and human 4-1BB by cultivating the transformed host cells. Antibodies that are immunoreactive with 4-1BB-L or human 4-1BB also are provided.

DETAILED DESCRIPTION OF THE INVENTION

Figure 1:
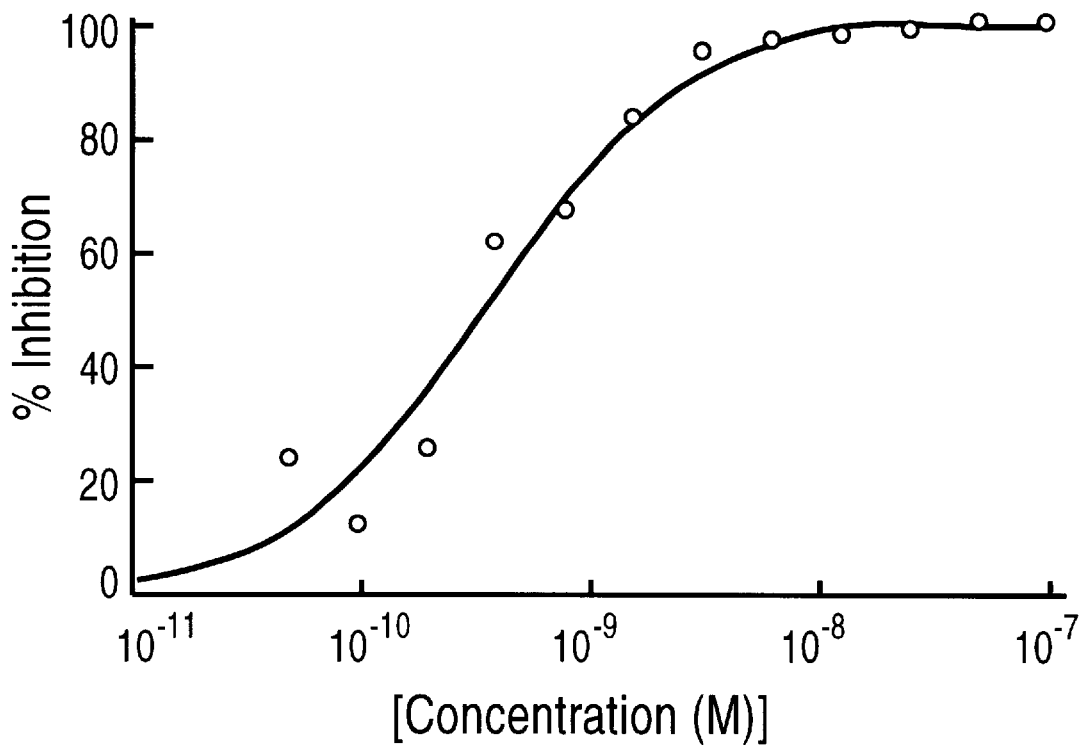
FIG. 1 presents the results of a competition binding assay that demonstrated binding of a murine 4-1BB/Fc fusion protein by a soluble murine 4-1BB-L protein produced in CV-1 (mammalian) cells. The 4-1BB-L protein was produced as described in example 7.

The present invention provides a human cell surface receptor designated 4-1BB. Human 4-1BB is a member of the TNF receptor super-family, and is expressed on cells that include but are not limited to stimulated human peripheral blood lymphocytes. Expression of murine 4-1BB on cell types that include helper, suppressor and cytolytic T lymphocytes has been reported (Kwon et al. I and II), and 4-1BB has also been detected on mouse brain tissue.

A novel cytokine designated 4-1BB ligand (4-1BB-L) is also provided herein. 4-1BB-L polypeptides bind to the cell surface receptor designated 4-1BB. Expression of 4-1BB-L has been detected on stimulated T cells (e.g., the alloreactive CD4+ human T cell clone stimulated with anti-CD3 antibodies described in example 5), a subclone of a mouse thymoma cell line, mouse brain tissue, and (by RNA analysis) on mouse bone marrow, splenic, and thymic tissues.

Purified 4-1BB-L polypeptides, exemplified by the murine and human 4-1BB-L proteins disclosed herein, and purified human 4-1BB polypeptides are encompassed by the present invention. Isolated DNA sequences encoding 4-1BB-L or human 4-1BB, recombinant expression vectors comprising the isolated DNA, and host cells transformed with the expression vectors are provided by the present invention, along with methods for producing 4-1BB-L and human 4-1BB by cultivating the transformed host cells and purifying the recombinant protein. Antibodies that are immunoreactive with 4-1BB-L or human 4-1BB are also disclosed.

The present invention provides full length 4-1BB-L and 4-1BB polypeptides as well as biologically active fragments and variants thereof. Soluble polypeptides comprising the extracellular domain of 4-1BB-L or a receptor-binding fragment thereof are among the biologically active fragments provided. Likewise, soluble polypeptides derived from the extracellular domain of human 4-1BB that are capable of binding the 4-1BB ligand are encompassed by the present invention. Such soluble polypeptides are described in more detail below.

4-1BB-L refers to a genus of mammalian polypeptides that are capable of binding 4-1BB. 4-1BB-L is a type II extracellular membrane polypeptide with an intracellular (cytoplasmic) domain at the N-terminus of the polypeptide, followed by a transmembrane region, and an extracellular (receptor-binding) domain at the C-terminus of the polypeptide. Soluble 4-1BB-L polypeptides may be derived from the extracellular domain, as described below. While not wishing to be bound by theory, binding of the 4-1BB ligand to 4-1BB may initiate transduction of a biological signal in a cell bearing the receptor.

cDNA encoding murine 4-1BB-L was isolated using a direct expression cloning technique, as described in example 4. Briefly, a fusion protein comprising a fragment of the murine 4-1BB extracellular (ligand-binding) domain fused to the Fc domain of a human IgG1 antibody was prepared and used to screen an expression cloning cDNA library derived from a subclone of a mouse thymoma cell line. A clone expressing a protein that bound the 4-1BB/Fc fusion protein was identified, sequenced and determined to encode a novel protein, which is a ligand for 4-1BB. The nucleotide sequence of the murine 4-1BB-L cDNA isolated by this procedure and the amino acid sequence encoded thereby are presented in SEQ ID NO:1 and SEQ ID NO:2. This murine 4-1BB-L protein comprises a cytoplasmic domain (amino acids 1–82 of SEQ ID NO:2), a transmembrane region (amino acids 83–103), and an extracellular domain (amino acids 104–309).

A direct expression cloning technique also was used to isolate cDNA encoding a human 4-1BB-L, as described in example 5. Briefly, an expression cloning cDNA library derived from an alloreactive CD4+ human T cell clone stimulated with an anti-CD3 antibody was screened with a fusion protein comprising a soluble human 4-1BB polypeptide fused to an Fc polypeptide. The nucleotide sequence of a human 4-1BB-L cDNA isolated by this procedure and the amino acid sequence encoded thereby are presented in SEQ ID NO:3 and SEQ ID NO:4. This human 4-1BB-L protein comprises a cytoplasmic domain (amino acids 1–25 of SEQ ID NO:4), a transmembrane region (amino acids 26–48), and an extracellular domain (amino acids 49–254).

The nucleotide sequence of a human 4-1BB cDNA (isolated as described in example 2) and the amino acid sequence encoded thereby are presented in SEQ ID NO:7 and SEQ ID NO:8. The human 4-1BB protein comprises an N-terminal signal sequence (amino acids −23 to −1 of SEQ ID NO:8), an extracellular domain comprising amino acids 1–163, a transmembrane region comprising amino acids 164–190, and a cytoplasmic domain comprising amino acids 191–232. The human 4-1BB amino acid sequence of SEQ ID NO:8 is 60% identical to that of the murine 4-1BB receptor described in Kwon et al. (*Proc. Natl. Acad. Sci. USA* 86:1963, 1989).

Also encompassed by the present invention are isolated DNA sequences that are degenerate as a result of the genetic code to the nucleotide sequence of SEQ ID NOS:1, 3, or 7 (and thus encode the amino acid sequence presented in SEQ ID NOS: 2, 4, or 8). The 4-1BB-L nucleotide sequences of SEQ ID NOS:1, 3, or 7 are understood to include the sequences complementary thereto.

Purified human 4-1BB-L proteins characterized by the N-terminal amino acid sequence Met-Glu-Tyr-Ala-Ser-Asp-Ala-Ser-Leu-Asp-Pro-Glu- (amino acids 1–12 of SEQ ID NO:4) or (beginning with the first amino acid of the extracellular domain) Leu-Ala-Cys-Pro-Trp-Ala-Val-Ser-Gly-Ala-Arg-Ala-Ser- (amino acids 49–61 of SEQ ID NO:4) are provided herein. Purified murine 4-1BB-L proteins characterized by an N-terminal amino acid sequence selected from the group consisting of Met-Asp-Gln-His-Thr-Leu-Asp-Val-Glu-Asp-Thr-Ala- (amino acids 1–12 of SEQ ID NO:2), or (beginning with one of the first three amino acids of the extracellular domain) Arg-Thr-Glu-Pro-Arg-Pro-Ala-Leu-Thr-Ile-Thr-Thr- (amino acids 104–115 of SEQ ID NO:2), Thr-Glu-Pro-Arg-Pro-Ala-Leu-Thr-Ile-Thr-Thr- (amino acids 105–115 of SEQ ID NO:2), and Glu-Pro-Arg-Pro-Ala-Leu-Thr-Ile-Thr-Thr- (amino acids 106–115 of SEQ ID NO:2) are also disclosed herein.

Soluble Proteins and Multimeric Forms of the Inventive Proteins

Soluble forms of the 4-1BB-L and 4-1BB proteins are provided herein. Soluble 4-1BB-L or 4-1BB polypeptides comprise all or part of the extracellular domain but lack the transmembrane region that would cause retention of the polypeptide on a cell membrane. The soluble polypeptides that may be employed retain the ability to bind 4-1BB. The soluble 4-1BB polypeptides that may be employed retain the ability to bind the 4-1BB ligand. The soluble proteins may include part of the transmembrane region or part of the cytoplasmic domain, provided that the protein is capable of being secreted rather than retained on the cell surface.

Since the 4-1BB-L protein lacks a signal peptide, a heterologous signal peptide advantageously is fused to the N-terminus of soluble 4-1BB-L polypeptides to promote secretion thereof. The signal peptide is cleaved from the protein upon secretion from the host cell. The need to lyse the cells and recover the recombinant soluble protein from the cytoplasm thus is avoided. The native signal peptide or a heterologous signal peptide (such as one of the heterologous signal peptides described below, chosen according to the intended expression system) advantageously is fused to a soluble 4-1BB polypeptide.

Soluble proteins of the present invention may be identified (and distinguished from their non-soluble membrane-bound counterparts) by separating intact cells expressing the desired protein from the culture medium, e.g., by centrifugation, and assaying the medium (supernatant) for the presence of the desired protein. The culture medium may be assayed using procedures which are similar or identical to those described in the examples below.

Soluble forms of the 4-1BB-L and 4-1BB proteins are advantageous for certain applications, e.g., when the protein is to be administered intravenously for certain therapeutic purposes. Also, purification of the proteins from recombinant host cells is facilitated, since the soluble proteins are secreted from the cells. In one embodiment of the invention, a soluble fusion protein comprises a first polypeptide derived from the extracellular domain of 4-1BB or 4-1BB-L fused to a second polypeptide added for purposes such as facilitating purification or effecting dimer formation. Suitable second polypeptides do not inhibit secretion of the soluble fusion protein.

Examples of soluble polypeptides include those comprising the entire extracellular domain. Representative examples of the soluble proteins of the present invention include, but are not limited to, a polypeptide comprising amino acids x-309 of SEQ ID NO:2, wherein x is selected from 104, 105, and 106 (murine 4-1BB-L); amino acids 49–254 of SEQ.ID NO:4 (human 4-1BB-L); or amino acids 1–163 of SEQ ID NO:8 (human 4-1BB). Preparation of certain soluble polypeptides of the present invention is described in the examples section.

Truncated forms of the inventive proteins, including soluble polypeptides, may be prepared by any of a number of conventional techniques. In the case of recombinant proteins, a DNA fragment encoding a desired fragment may be subcloned into an expression vector. Alternatively, a desired DNA sequence may be chemically synthesized using known techniques. DNA fragments also may be produced by restriction endonuclease digestion of a full length cloned DNA sequence, and isolated by electrophoresis on agarose gels. Linkers containing restriction endonuclease cleavage site(s) may be employed to insert the desired DNA fragment into an expression vector, or the fragment may be digested at cleavage sites naturally present therein. The well known polymerase chain reaction procedure also may be employed to isolate a DNA sequence encoding a desired protein fragment by using oligonucleotide primers comprising sequences that define the termini of the desired fragment.

In another approach, enzymatic treatment (e.g., using Bal 31 exonuclease) may be employed to delete terminal nucleotides from a DNA fragment to obtain a fragment having a particular desired terminus. Among the commercially available linkers are those that can be ligated to the blunt ends produced by Bal 31 digestion, and which contain restriction endonuclease cleavage site(s). Alternatively, oligonucleotides that reconstruct the N- or C-terminus of a DNA fragment to a desired point may be synthesized. The oligonucleotide may contain a restriction endonuclease cleavage site upstream of the desired coding sequence and position an initiation codon (ATG) at the N-terminus of the coding sequence, present therein. The well known polymerase chain reaction procedure also may be employed to isolate a DNA sequence encoding a desired protein fragment by using oligonucleotide primers comprising sequences that define the termini of the desired fragment.

Naturally occurring soluble forms of 4-1BB-L or human 4-1BB are also encompassed by the present invention. Such soluble polypeptides may result from alternative splicing of mRNA during expression, or release of a soluble polypeptide from a membrane-bound form of the protein by proteolysis.

Oligomeric (multimeric) forms of the inventive proteins are encompassed by the present invention. The terms "inventive proteins" and "inventive polypeptides" as used herein refer collectively to the 4-1BB-L and 4-1BB proteins or polypeptides of the present invention, as defined by the appended claims. The oligomers preferably are dimers or trimers. Dimeric and trimeric forms of the 4-1BB-L and 4-1BB proteins may exhibit enhanced biological activity compared to the monomeric forms. Separate polypeptide chains may be joined by interchain disulfide bonds formed between cysteine residues to form oligomers. Alternatively, the multimers may be expressed as fusion proteins, with or without spacer amino acids between the inventive protein moieties, using recombinant DNA techniques. In one embodiment of the present invention, two or three soluble 4-1BB-L or 4-1BB polypeptides are joined via a polypeptide linker (e.g., one of the antibody-derived or peptide linkers described below).

In one embodiment of the present invention, a soluble fusion protein comprises a soluble 4-1BB or 4-1BB-L polypeptide fused to a polypeptide derived from the constant region of an antibody. Multimers resulting from formation of interchain disulfide bonds between the antibody-derived moieties of such fusion proteins are provided.

Examples of such fusion proteins are those comprising one of the above-described soluble 4-1BB or 4-1BB-L polypeptides fused to an antibody Fc region polypeptide. A gene fusion encoding the fusion protein is inserted into an appropriate expression vector and cells transformed with the expression vector are cultured to produce and secrete the fusion protein. The expressed fusion proteins are allowed to assemble much like antibody molecules, whereupon interchain disulfide bonds form between Fc polypeptides, yielding the Fc/4-1BB-L or 4-1BB/Fc protein in dimeric form. The preparation of certain embodiments of such fusion proteins and dimers formed therefrom is described in more detail in the examples section below. If two different fusion proteins are made, one comprising an inventive protein fused to the heavy chain of an antibody and the other comprising an inventive protein fused to the light chain of an antibody, it is possible to form oligomers comprising as many as four soluble inventive polypeptides.

Preparation of fusion proteins comprising heterologous polypeptides fused to various portions of antibody-derived polypeptides (including the Fc domain) has been described, e.g., by Ashkenazi et al. (*PNAS USA* 88:10535, 1991) and Byrn et al. (*Nature* 344:677, 1990). The term "Fc polypeptide" includes native and mutein forms, as well as truncated Fc polypeptides containing the hinge region that promotes dimerization. One example is an Fc region encoded by cDNA obtained by PCR as described by Fanslow et al., *J. Immunol.* 149:65 (1992). One example of a DNA encoding a mutein of the Fc region of a human IgG1 antibody is described in U.S. patent application Ser. No. 08/097,827, entitled "Novel Cytokine Which is a Ligand for OX40" filed Jul. 23, 1993, which application is hereby incorporated by reference. The mutein DNA was derived from a native Fc polypeptide-encoding DNA by site-directed mutagenesis conducted essentially as described by Deng and Nickoloff, *Anal. Biochem.* 200:81 (1992). The amino acid sequence of the Fc mutein polypeptide is identical to that of the native Fc polypeptide presented in SEQ ID NO:15 except that amino acid 32 of SEQ ID NO:15 has been changed from Leu to Ala, amino acid 33 has been changed from Leu to Glu, and amino acid 35 has been changed from Gly to Ala. This mutein Fc exhibits reduced affinity for immunoglobulin receptors.

Alternatively, one can link multiple copies of the inventive proteins via peptide linkers. A fusion protein comprising two or more copies of the inventive protein, separated by peptide linkers, may be produced by recombinant DNA technology. Among the peptide linkers that may be employed are amino acid chains that are from 5 to 100 amino acids in length, preferably comprising amino acids selected from the group consisting of glycine, asparagine, serine, threonine, and alanine. In one embodiment of the present invention, a fusion protein comprises two or three soluble 4-1BB-L or 4-1BB polypeptides linked via a peptide linker selected from Gly$_4$SerGly$_5$Ser (SEQ ID NO:17) and (Gly$_4$Ser)$_n$ (SEQ ID NO:18), wherein n is 4–12. The production of recombinant fusion proteins comprising peptide linkers is illustrated in U.S. Pat. No. 5,073,627, for example.

The 4-1BB-L proteins of the present invention are believed to be capable of dimerization without having one of the above-described antibody-derived polypeptides fused to the ligand. Both soluble and full length recombinant 4-1BB-L proteins have been precipitated with 4-1BB/Fc (reductive immunoprecipitation) followed by purification by affinity chromatography on a column containing protein G. Dimers were detected by SDS-PAGE (non-reducing gel). Higher oligomers may have formed as well. Thus, fusing polypeptides that promote dimerization (or formation of higher oligomers) to 4-1BB ligands may result in undesirable aggregate formation.

Variants and Derivatives

As used herein, the terms "4-1BB-L" and "human 4-1BB" include variants and derivatives that retain a desired biological activity of the native mammalian polypeptides. The variant sequences differ from a native nucleotide or amino acid sequence by one or a plurality of substitutions, deletions, or additions, but retain a desired biological activity such as the ability to bind 4-1BB (for variants of 4-1BB-L) or the ability to bind a 4-1BB-L (for variants of 4-1BB, the receptor). Derivatives of the inventive proteins may comprise moieties such as the chemical moieties described below, attached to the inventive protein.

In one embodiment of the present invention, a variant sequence is substantially identical to a native sequence. The term "substantially identical" as used herein means that the amino acid or nucleotide sequence in question is at least 80% identical, preferably 90–100% identical, to a reference (native) sequence. The degree of homology (percent identity) may be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure,* National Biomedical Research Foundation, pp. 353–358, 1979; (2) a penalty of 3.0 for each gap and an additional 0.10 penalty for each symbol in each gap; and (3) no penalty for end gaps.

Alterations of the native amino acid sequence may be accomplished by any of a number of known techniques, e.g., by mutation of the native nucleotide sequences disclosed herein. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures such as those described by Walder et al. (*Gene* 42:133, 1986); Bauer et al. (*Gene* 37:73, 1985); Craik (*BioTechniques,* January 1985, 12–19); Smith et al. (*Genetic Engineering: Principles and Methods,* Plenum Press, 1981); and U.S. Pat. Nos. 4,518,584 and 4,737,462, may be employed.

Isolated DNA sequences that hybridize to the murine 4-1BB-L-encoding nucleotide sequence of SEQ ID NO:1 or the human 4-1BB-L-encoding nucleotide sequence of SEQ ID NO:3 under moderately stringent or severely stringent conditions are encompassed by the present invention. Moderate stringency conditions refer to conditions described in, for example, Sambrook et al. *Molecular Cloning: A Laboratory Manual,* 2 ed. Vol. 1, pp. 1.101–104, Cold Spring Harbor Laboratory Press, (1989). Conditions of moderate stringency, as defined by Sambrook et al., include prewashing in 5×SSC, 0.5% SDS, 1.0 mM EDTA (pH 8.0) and hybridization at about 55° C. in 5×SSC overnight. Conditions of severe stringency include higher temperatures of hybridization and washing. The skilled artisan recognizes that the temperature and wash solution salt concentration may be adjusted as necessary according to factors such as the length of the probe. One embodiment of the invention is directed to DNA sequences that will hybridize under severely stringent conditions to a DNA sequence comprising the coding region of a 4-1BB-L clone disclosed herein. The severely stringent conditions include hybridization at 68° C. followed by washing in 0.1×SSC/0.1% SDS at 63–68° C.

Among the hybridizing sequences encompassed by the present invention are those encoding a biologically active primate or murine 4-1BB-L polypeptides. Biologically active polypeptides encoded by DNA sequences that hybridize to the murine 4-1BB-L-encoding nucleotide sequence of SEQ ID NO:1 or the human 4-1BB-L-encoding nucleotide sequence of SEQ ID NO:3 under moderately stringent or severely stringent conditions are encompassed by the present invention.

In one embodiment of the present invention, a variant amino acid sequence comprises conservative amino acid substitution(s) but is otherwise identical to a native amino acid sequence. Conservative substitutions refer to replacement of a given amino acid residue with a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known.

The present invention further includes the inventive polypeptides with or without associated native-pattern glycosylation. The recombinant proteins when expressed in yeast or mammalian expression systems (e.g., COS-7 cells) may be similar or significantly different in molecular weight and glycosylation pattern than the corresponding native proteins. Expression of mammalian 4-1BB-L polypeptides in bacterial expression systems such as *E. coli,* provides non-glycosylated molecules.

Variant proteins comprising inactivated N-glycosylation sites are within the scope of the present invention. Such variants are expressed in a more homogeneous, reduced carbohydrate form. N-glycosylation sites in eukaryotic polypeptides are characterized by an amino acid triplet Asn-X-Y, wherein X is any amino acid except Pro and Y is Ser or Thr. In this sequence, carbohydrate residues are covalently attached at the Asn side chain. Addition, substitution, or deletion of residue(s) so that the Asn-X-Y triplet is no longer present inactivates the site. In one embodiment, a conservative amino acid substitution replaces the Asn residue, with substitution of Asp, Gln, or Glu for Asn being preferred. Known procedures for inactivating N-glycosylation sites in proteins include those described in U.S. Pat. No. 5,071,972 and EP 276,846.

The murine 4-1BB-L of SEQ ID NO:2 comprises three N-glycosylation sites, at residues 139–141, 161–163, and 293–295. The human 4-1BB-L of SEQ ID NO:4 comprises no N-glycosylation sites. The human 4-1BB of SEQ ID NO:8 comprises two such sites, at residues 115–117 and 126–128.

Naturally occurring variants such as those resulting from alternative mRNA splicing events or proteolytic cleavage are also within the scope of the present invention. Variations attributable to proteolysis include, for example, differences in the N- or C-termini upon expression in different types of host cells, due to proteolytic removal of one or more terminal amino acids (which may occur intracellularly or during purification). In one embodiment of the present invention, the inventive proteins lack from one to five of the N- or C-terminal amino acids of the sequences disclosed herein. In certain host cells, post-translational processing will remove the methionine residue encoded by an initiation codon, whereas the methionine residue will remain at the N-terminus of proteins produced in other host cells.

Additional variants may be prepared by deleting terminal or internal sequences not needed for biological activity. For example, Cys residues can be deleted or replaced with other amino acids to prevent formation of incorrect intramolecular disulfide bridges upon renaturation.

Other variants are prepared by modifying KEX2 protease processing sites in the inventive proteins to enhance expression in yeast cells in which KEX2 protease activity is present. The adjacent basic residue pairs that constitute KEX2 protease processing sites, and are to be inactivated by adding, substituting or deleting residue(s), are Arg-Arg, Arg-Lys, and Lys-Arg pairs. Lys-Lys pairs are considerably less susceptible to KEX2 cleavage, and conversion of Arg-Arg, Arg-Lys, and Lys-Arg pairs to a Lys-Lys doublet is a conservative and preferred alteration that essentially inactivates the KEX2 sites. EP 212,914 discloses the use of site-specific mutagenesis to inactivate KEX2 protease processing sites in a protein.

The inventive proteins may be modified by forming covalent or aggregative conjugates with other chemical moieties, such as glycosyl groups, lipids, phosphate, acetyl groups and the like. Covalent derivatives are prepared by reaction of functional groups of the chemical moiety with functional groups on amino acid side chains or at the N-terminus or C-terminus of the inventive protein. Also provided herein are the inventive proteins comprising detectable labels, diagnostic or cytotoxic reagents attached thereto, including but not limited to radionuclides, colorimetric reagents, and the like.

Other derivatives within the scope of this invention include covalent or aggregative conjugates of the inventive proteins or fragments thereof with other proteins or polypeptides, such as by synthesis in recombinant culture as N-terminal or C-terminal fusions. The inventive proteins can comprise polypeptides added to facilitate purification and identification (e.g., the antigenic identification peptides described in U.S. Pat. No. 5,011,912 and Hopp et al., *Bio/Technology* 6:1204, 1988; or a poly-His peptide). One such peptide is the FLAG® peptide DYKDDDDK (SEQ ID NO:16), which is a highly antigenic sequence that provides an epitope reversibly bound by a specific monoclonal antibody (e.g., the monoclonal antibody produced by the hybridoma designated 4E11 and deposited with the American Type Culture Collection under accession no. HB 9259) to enable rapid assay and facilitate purification of the expressed recombinant polypeptide fused thereto.

Assays for Biological Activity

The 4-1BB-L and 4-1BB proteins of the present invention and variants and derivatives thereof may be tested for biological activity by any suitable assay procedure. The procedure will vary according to such factors as whether the protein to be tested is bound to a cell surface or is secreted into the culture supernatant. Proteins may be radiolabeled for use in the assays, e.g., using the commercially available IODO-GEN reagent described in example 1.

Competitive binding assays can be performed using standard methodology. For example, a 4-1BB-L variant can be tested for the ability to compete with a radiolabeled 4-1BB-L protein for binding to cells that express 4-1BB on the cell surface. Likewise, a 4-1BB variant can be assayed for the ability to compete with a radiolabeled 4-1BB for binding to cells expressing membrane-bound 4-1BB-L. Qualitative results can be obtained by competitive autoradiographic plate binding assays, or Scatchard plots may be utilized to generate quantitative results. Instead of intact cells, one could substitute a 4-1BB or 4-1BB-L protein bound to a solid phase such as a column chromatography matrix (e.g. a soluble 4-1BB/Fc fusion protein bound to a Protein A or Protein G column by interaction with the Fc region of the fusion protein).

Intact cells employed in competition binding assays may be cells that naturally express 4-1BB-L or 4-1BB (e.g., cell types identified in the examples below). Alternatively, cells transfected with recombinant expression vectors such that the cells express 4-1BB-L or 4-1BB.

One assay technique useful for intact cells expressing a membrane-bound form of the protein in question is the phthalate oil separation method (Dower et al. *J. Immunol.* 132:751 (1984)), essentially as described by Park et al. (*J. Biol. Chem.* 261:4177 (1986)). Sodium azide (0.2%) can be included in a binding assay to inhibit internalization of 4-1BB-L by the cells. Cells expressing 4-1BB on their surface can be tested for radiolabeled 4-1BB-L binding by a plate binding assay as described in Sims et al., *Science* 241:585 (1988).

Expression Systems

The present invention provides recombinant expression vectors for expression of the proteins of the present invention and host cells transformed with the expression vectors. Any suitable expression system may be employed.

Recombinant expression vectors of the present invention comprise DNA encoding a 4-1BB-L polypeptide or a human 4-1BB polypeptide, operably linked to regulatory sequence (s) suitable for expression of said DNA sequence in a host cell. The 4-1BB-L or 4-1BB-encoding DNA may comprise cDNA, genomic DNA, chemically synthesized DNA, DNA isolated by PCR, or combinations thereof. The regulatory sequences may be derived from sources that include, but are not limited to, mammalian, microbial, viral, or insect genes. Examples of regulatory sequences include promoters, operators, and enhancers, ribosomal binding sites, and appropriate sequences that control transcription and translation initiation and termination. Nucleotide sequences are operably linked when the regulatory sequence functionally relates to the structural gene. For example, a promoter sequence is operably linked to a coding sequence (e.g. structural gene DNA) if the promoter controls the transcription of the structural gene.

Suitable host cells for expression of the inventive proteins include prokaryotes, yeast or higher eukaryotic cells, with mammalian cells being preferred. The recombinant expression vectors are transfected into the host cells by conventional techniques. The transfected cells are cultivated under conditions suitable to effect expression of the desired recombinant protein, which is purified from the cells or culture medium, depending on the nature of the culture system and the expressed protein. As will be readily appreciated by the skilled artisan, cultivation conditions will vary according to factors that include the type of host cell and particular expression vector employed. Cell-free in vitro translation systems could also be employed to produce the inventive proteins by translation of mRNA complementary to a nucleotide sequence disclosed herein.

Appropriate cloning and expression vectors for use with bacterial, fungal, yeast, and mammalian cellular hosts are described, for example, in Pouwels et al. *Cloning Vectors: A Laboratory Manual,* Elsevier, N.Y., (1985). Expression vectors generally comprise one or more phenotypic selectable markers (e.g., a gene encoding a protein that confers antibiotic resistance or that supplies an autotrophic requirement) and an origin of replication recognized by the intended host cell to ensure amplification within the host.

Certain prokaryotic expression vectors may be constructed by inserting a promoter and other desired regulatory sequences into a commercially available plasmid such as the cloning vector pBR322 (ATCC 37017). pBR322 contains genes for ampicillin and tetracycline resistance and thus provides simple means for identifying transformed cells. Promoters commonly employed in prokaryotic expression vectors include β-lactamase (penicillinase), the lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36,776) and tac promoter (Maniatis, *Molecular Cloning: A Laboratory Manual,* Cold Spring Harbor Laboratory, p. 412, 1982). A particularly useful prokaryotic host cell expression system employs a phage λ $P_L$ promoter and a cI857ts thermolabile repressor sequence. Plasmid vectors available from the American Type Culture Collection which incorporate derivatives of the λ $P_L$ promoter include plasmid pHUB2 (resident in *E. coli* strain JMB9 (ATCC 37092)) and pPLc28 (resident in *E. coli* RR1 (ATCC 53082)).

The inventive proteins may be expressed in yeast host cells, preferably from the *Saccharomyces* genus (e.g., *S. cerevisiae*). Other genera of yeast, such as Pichia or Kluyveromyces, may also be employed. Yeast vectors commonly contain an origin of replication from a 2μ yeast plasmid, an autonomously replicating sequence (ARS), a promoter region, sequences for polyadenylation, sequences for transcription termination, and a selectable marker. Suitable promoter sequences for yeast vectors include promoters for metallothionein, 3-phosphoglycerate kinase (Hitzeman et al., *J. Biol. Chem.* 255:2073 (1980) or other glycolytic enzymes (Hess et al., *J. Adv. Enzyme Reg.* 7:149 (1968) and Holland et al., *Biochem.* 17:4900 (1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. The ADH2 promoter has been described by Russell et al. (*J. Biol. Chem.* 258:2674 (1982)) and Beier et al. (*Nature* 300:724 (1982)). Other suitable vectors and promoters for use in yeast expression are further described in Hitzeman, EPA-73,657. The vector may comprise a sequence encoding the yeast α-factor leader to direct secretion of a heterologous protein (an inventive protein) fused thereto. See Kurjan et al., *Cell* 30:933, 1982; and Bitter et al., *Proc. Natl. Acad. Sci. USA* 81:5330, 1984.

Shuttle vectors replicable in more than one type of cell comprise multiple origins of replication and selective markers. For example, a shuttle vector that replicates in both yeast and *E. coli* and functions as an expression vector in yeast may comprise DNA sequences from pBR322 for selection and replication in *E. coli* ($Amp^r$ gene and origin of replication) and yeast-derived sequences such as a glucose-repressible ADH2 promoter, an origin of replication from a 2μ yeast plasmid, and an α-factor leader sequence.

Yeast transformation protocols are known to those of skill in the art. One such protocol is described by Hinnen et al., *Proc. Natl. Acad. Sci. USA* 75:1929 (1978). The Hinnen et al. protocol selects for $Trp^+$ transformants in a selective medium, wherein the selective medium consists of 0.67% yeast nitrogen base, 0.5% casamino acids, 2% glucose, 10 μg/ml adenine and 20 μg/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 μg/ml adenine and 80 μg/ml uracil. Derepression of the ADH2 promoter occurs when glucose is exhausted from the medium.

Mammalian or insect host cell culture systems could also be employed to express the recombinant proteins of the present invention. Examples of suitable mammalian host cell lines include the COS-7 lines of monkey kidney cells (ATCC CRL 1651) (Gluzman et al., *Cell* 23:175 (1981)), L cells, C127 cells, 3T3 cells (ATCC CCL 163), Chinese hamster ovary (CHO) cells, HeLa cells, CV-1 cells, CV-1/EBNA cells and BHK (ATCC CRL 10) cell lines. Suitable mammalian expression vectors generally include nontranscribed elements such as an origin of replication, a promoter sequence, an enhancer linked to the structural gene, other 5' or 3' flanking nontranscribed sequences, such as ribosome binding sites, a polyadenylation site, splice donor and acceptor sites, and transcriptional termination sequences.

Transcriptional and translational control sequences in mammalian host cell expression vectors may be provided by viral sources. For example, commonly used mammalian cell promoter sequences and enhancer sequences are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a structural gene sequence in a mammalian host cell. Viral early and late promoters are particularly useful because both are easily obtained from a viral genome as a fragment which may also contain a viral origin of replication (Fiers et al., *Nature* 273:113 (1978)). Smaller or larger SV40 fragments may also be used, provided the approximately 250 bp sequence extending from the Hind III site toward the Bgl I site located in the SV40 viral origin of replication site is included.

Exemplary mammalian expression vectors can be constructed as disclosed by Okayama and Berg.(*Mol. Cell. Biol.* 3:280 (1983)). A useful high expression vector, PMLSV N1/N4, described by Cosman et al., *Nature* 312:768 (1984) has been deposited as ATCC 39890. A vector designated pHAVEO is described by Dower et al., *J. Immunol.* 142:4314 (1989). Certain useful mammalian expression vectors are described in the examples section below.

The vectors additionally may contain a DNA sequence encoding a signal peptide (secretory leader) fused to the 5' end of a DNA sequence encoding one of the inventive polypeptides. The 4-1BB-L polypeptides lack a native signal sequence. Replacement of the native human 4-1BB signal sequence with a heterologous signal sequence may be desirable to enhance expression levels in the particular host cells employed. Examples of heterologous signal peptides that may be employed are the human or murine interleukin-7 signal peptide described in U.S. Pat. No. 4,965,195; the interleukin-2 signal peptide described in Cosman et al. *Nature* 312:768, 1984; and the interleukin-4 signal peptide described in EP 367,566.

Purification of Recombinant Mammalian 4-1BB-L

The present invention provides substantially homogeneous 4-1BB-L and human 4-1BB proteins, which may be produced by recombinant expression systems or purified from naturally occurring cellular sources. The proteins are purified to substantial homogeneity, as indicated by a single protein band upon analysis by SDS-polyacrylamide gel electrophoresis (SDS-PAGE).

Recombinant 4-1BB or 4-1BB-L proteins may be produced as follows. Host cells are transformed with an expression vector containing DNA encoding an inventive polypeptide, wherein the DNA is operably linked to regulatory sequences suitable for effecting expression of said inventive polypeptide in the particular host cells. The transformed host cells are cultured under conditions that promote expression of the 4-1BB-L or 4-1BB polypeptide, which is then purified from the culture media or cell extracts. The purification procedure will vary according to such factors as the particular host cells employed and whether the expressed protein is secreted or membrane-bound, as the skilled artisan will readily appreciate.

Recombinant protein produced in bacterial culture is usually isolated by initial disruption of the host cells, centrifugation, extraction from cell pellets if the desired protein is in the form of an insoluble refractile body, or from the supernatant if a soluble polypeptide, followed by one or more concentration, salting-out, ion exchange or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Recombinant polypeptides secreted from yeast cells can be purified by methods analogous to those disclosed by Urdal et al. (*J. Chromatog.* 296:171 (1984)). Urdal et al. describe two sequential, reversed-phase HPLC steps for purification of recombinant human IL-2 on a preparative HPLC column.

The purification procedure may involve affinity chromatography. A 4-1BB-L protein (or the extracellular domain thereof) may be attached to a solid support material by standard procedures for use in purifying a 4-1BB protein. Likewise, a 4-1BB protein (or the extracellular domain thereof) attached to a solid support material may be used in purifying a 4-1BB-L protein. In addition, 4-1BB-L/Fc or 4-1BB/Fc fusion proteins may be attached to Protein G- or Protein A-bearing chromatography columns via binding of the Fc moiety to the Protein A or Protein G. Immunoaffinity columns comprising an antibody that binds the desired inventive protein (described in example 8) also may be employed.

In one purification procedure, a 4-1BB-L or 4-1BB polypeptide is concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred.

Finally, one or more reverse-phase high performance liquid chromatography (RP-HPLC) steps employing hydrophobic RP-HPLC media, (e.g., silica gel having pendant methyl or other aliphatic groups) can be employed to further purify 4-1BB-L. Some or all of the foregoing purification steps, in various combinations, can also be employed to provide a substantially homogeneous recombinant protein.

Pharmaceutical Compositions Comprising the Inventive Polypeptides and Uses of 4-1BB-L and 4-1BB DNA and Proteins The 4-1BB and 4-1BB-L proteins of the present invention are expressed on cells that include certain types of T-lymphocytes, as discussed above and in the examples section. The inventive proteins thus are useful in exploring mechanisms of T-cell activation. Identifying novel proteins expressed on T-cells, such as the inventive proteins disclosed herein, has important implications in furthering understanding of the regulation and function of the immune system.

Murine 4-1BB and 4-1BB-L also have been detected on brain tissue. Northern blot analysis revealed expression of human 4-1BB-L in brain, and human 4-1BB is expected to be expressed in the brain as well. The inventive proteins are useful reagents for studying neural tissue, e.g., research into growth of neural cells and disorders of the brain.

The 4-1BB-L of the present invention also has been found to stimulate growth of $CD3^-$ $CD4^-$ $CD8^-$ immature lymphocytes. Cells expressing a membrane-bound 4-1BB-L were cultivated with $CD3^-$ $CD4^-$ $CD8^-$ immature lymphocytes, and growth of the lymphocytes was stimulated.

As described in example 13, cells expressing recombinant human 4-1BB-L induced a strong proliferative response in mitogen costimulated peripheral blood T-cells. In contrast, the ligand enhanced cytolysis seen in costimulated long-term cultured T-cell clones.

Uses of 4-1BB-L that flow from this ligand's ability to co-stimulate T-cell proliferation include, but are not limited to, the following. 4-1BB-L finds use as a tissue culture reagent for the in vitro cultivation of primary T-cells, and during the derivation of clonal T-cell lines therefrom. The ligand also may be employed to stimulate proliferation of activated T-cells that are to be employed in therapeutic procedures. For example, T-cells may be removed from a cancer patient and cultivated in the presence of a tumor antigen in vitro by known procedures, to generate cytotoxic T-lymphocytes (CTLs) specific for the patient's tumor cells. The CTLs are then administered to the patient. To enhance proliferation of the CTLs in the ex vivo stage, 4-1BB-L may be added to the culture medium, either alone or in combination with other cytokines such as interleukin-2.

It has been suggested that elimination of peripheral T-cells by activation induced cytolysis may be an important mechanism of regulating unwanted or autoreactive T-cells (Owen-Schaub et al., *Cell. Immunol.* 140:197, 1992). 4-1BB-L enhanced cell death induced by mitogenic stimuli in a long-term cultured (chronically activated) T-cell clone. These data suggest that 4-1BB-L may play a role in this process by enhancing activation-induced cell death.

The 4-1BB-L of the present invention is useful as a research reagent in in vitro binding assays to detect cells expressing 4-1BB. For example, 4-1BB-L or a fragment thereof (e.g., the extracellular domain) can be labeled with a detectable moiety such as $^{125}$I. Alternatively, another detectable moiety such as biotin, avidin, or an enzyme that can catalyze a colorometric or fluorometric reaction may be used. Cells to be tested for 4-1BB expression are contacted with the labeled 4-1BB-L then washed to remove unbound labeled 4-1BB-L. Cells that bound the labeled 4-1BB-L are detected via the detectable moiety. Likewise, the human 4-1BB of the present invention is useful as a research reagent in binding assays to detect cells expressing 4-1BB-L. Identifying additional cell types expressing 4-1BB or 4-1BB-L provides insight into cell types that may play a role in the activation and function of cells of the immune system, particularly T-cells.

The 4-1BB ligand proteins disclosed herein also may be employed to measure the biological activity of 4-1BB protein in terms of binding affinity for 4-1BB-L. To illustrate, 4-1BB-L may be employed in a binding affinity study to measure the biological activity of a 4-1BB protein that has been stored at different temperatures, or produced in different cell types. The biological activity of a 4-1BB protein thus can be ascertained before it is used in a research study, for example.

4-1BB-L proteins find use as reagents that may be employed by those conducting "quality assurance" studies, e.g., to monitor shelf life and stability of 4-1BB protein under different conditions. 4-1BB ligands may be used in determining whether biological activity is retained after modification of a 4-1BB protein (e.g., chemical modification, truncation, mutation, etc.). The binding affinity of the modified 4-1BB protein for a 4-1BB-L is compared to that of an unmodified 4-1BB protein to detect any adverse impact of the modifications on biological activity of 4-1BB.

A different use of a 4-1BB ligand is as a reagent in protein purification procedures. 4-1BB-L or Fc/4-1BB-L fusion proteins may be attached to a solid support material by conventional techniques and used to purify 4-1BB by affinity chromatography.

Likewise, human 4-1BB may be employed to measure the biological activity of human 4-1BB-L polypeptides in terms of binding affinity. Human 4-1BB finds further use in purification of human 4-1BB-L by affinity chromatography.

The present invention provides pharmaceutical compositions comprising an effective amount of a purified 4-1BB-L or 4-1BB polypeptide and a suitable diluent, excipient, or carrier. Such carriers will be nontoxic to patients at the dosages and concentrations employed. Ordinarily, the preparation of such compositions entails combining a mammalian 4-1BB-L polypeptide or derivative thereof with buffers, antioxidants such as ascorbic acid, low molecular weight (less than about 10 residues) polypeptides, proteins, amino acids, carbohydrates including glucose, sucrose or dextrans, chelating agents such as EDTA, glutathione and other stabilizers and excipients. Neutral buffered saline or saline mixed with conspecific serum albumin are exemplary appropriate diluents.

Such compositions may be used to stimulate the immune system in view of the inventive proteins' presence and effect on certain cells associated with the immune response. For therapeutic use, the compositions are administered in a manner and dosage appropriate to the indication and the size and condition of the patient. Administration may be by injection, continuous infusion, sustained release from implants, or other suitable mode.

Nucleic Acid Fragments

The present invention further provides fragments of the 4-1BB-L and human 4-1BB nucleotide sequences presented herein. Such fragments desirably comprise at least about 14 nucleotides. DNA and RNA complements of said fragments are provided herein, along with both single-stranded and double-stranded forms of the DNA.

Among the uses of such nucleic acid fragments is use as a probe. Such probes may be employed in cross-species hybridization procedures to isolate 4-1BB-L or 4-1BB DNA from additional mammalian species. As one example, a probe corresponding to the extracellular domain of 4-1BB-L or 4-1BB may be employed. The probes also find use in detecting the presence of 4-1BB-L or 4-1BB nucleic acids in in vitro assays and in such procedures as Northern and Southern blots. Cell types expressing 4-1BB-L or 4-1BB can be identified. Such procedures are well known, and the skilled artisan can choose a probe of suitable length, depending on the particular intended application.

Other useful fragments of the 4-1BB-L or 4-1BB nucleic acids are antisense or sense molecules comprising a single-stranded nucleic acid sequence (either RNA or DNA) capable of binding to target 4-1BB-L or 4-1BB mRNA (sense) or DNA (antisense) sequences. In one embodiment, the antisense or sense molecule is a nucleotide sequence corresponding or complementary to the coding region of the 4-1BB or 4-1BB-L sequences presented herein or a fragment thereof or the RNA complement thereof. Such oligonucleotides preferably comprise at least about 14 nucleotides, most preferably from about 17 to about 30 nucleotides. The ability to derive an antisense or a sense oligonucleotide based upon a cDNA sequence for a given protein is described in, for example, Stein and Cohen, *Cancer Res.* 48:2659, 1988 and van der Krol et al., *BioTechniques* 6:958, 1988.

Binding of antisense or sense oligonucleotides to target nucleic acid sequences results in the formation of duplexes that block translation (RNA) or transcription (DNA) by one of several means, including enhanced degradation of the duplexes, premature termination of transcription or translation, or by other means. The antisense oligonucleotides thus may be used to block expression of 4-1BB-L proteins.

Antisense or sense oligonucleotides of the present invention further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences. Other examples of sense or antisense oligonucleotides include those oligonucleotides which are covalently linked to organic moieties, such as those described in WO 90/10448, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, CaPO$_4$-mediated DNA transfection, electroporation, or other gene transfer vectors such as Epstein-Barr virus. Antisense or sense oligonucleotides are preferably introduced into a cell containing the target nucleic acid sequence by insertion of the antisense or sense oligonucleotide into a suitable retroviral vector, then contacting the cell with the retrovirus vector containing the inserted sequence, either in vivo or ex vivo. Suitable retroviral vectors include, but are not limited to, vectors derived from the murine retrovirus M-MuLV, N2 (a retrovirus derived from M-MuLV), or the double copy vectors designated DCT5A, DCT5B and DCT5C (see PCT Application US 90/02656).

Sense or antisense oligonucleotides may also be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. The ligand binding molecule should be conjugated in a manner that does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

The following examples are for the purposes of illustrating certain embodiments of the invention, and are not to be construed as limiting the scope of the invention as claimed herein.

EXAMPLE 1

Preparation of Murine 4-1BB/Fc Fusion Protein for Use in Screening Clones

This example illustrates construction of an expression vector encoding a fusion protein comprising a soluble murine 4-1BB polypeptide fused to an Fc region polypeptide derived from a human IgG1 antibody. The fusion protein is used for detecting clones encoding a 4-1BB ligand. One advantage of employing an Fc-containing fusion protein is the facile purification made possible by the Fc moiety. Other polypeptides derived from an antibody Fc domain, and which bind with relatively high affinity to protein A- or protein G-containing columns, may be substituted for the Fc polypeptide employed below.

DNA encoding a portion of the extracellular (ligand binding) domain of the murine 4-1BB receptor was isolated by polymerase chain reaction (PCR) using primers based upon the sequence published in Kwon et al. II and presented herein as SEQ ID NOS:5 and 6. A BD14-20 alloreactive murine T-cell clone was induced with concanavalin A (Con A), using standard techniques (Kwon et al. II). Total RNA was isolated from the induced cells by the guanadinium thiocyanate method (Mosley et al., *Cell* 59: 335 (1989)). cDNA was prepared by conventional techniques and used as the template in a conventional PCR procedure (Sarki et al., *Science* 239:487, 1988). The 5' primer oligonucleotide sequence was:

GTCACTAGTTCT<u>GTGCAGAACTCCTGTG</u>
<u>ATAAC</u>    (SEQ ID NO:9)

SEQ ID NO:9 comprises a SpeI site (double underline) and a signal cleavage site followed by a sequence (underlined) that corresponds to the nucleotides encoding the first seven amino acids of the mature murine 4-1BB protein. The 3' primer sequence was a 35-mer oligonucleotide comprising the sequence:

CACAAGA<u>TCT</u>GGGCTC<u>CTCFGGAGTCAC</u>
<u>AGAAATG</u>    (SEQ ID NO:10)

The SEQ ID NO:10 oligonucleotide contains a Bgl 2 restriction site (double underline) and a sequence (underlined) that is complementary to nucleotides 510–528 of SEQ ID NO:5.

The PCR reaction was amplified with 30 cycles. The amplified DNA fragment comprised a sequence encoding a soluble murine 4-1BB polypeptide comprising amino acids 1 (Val) through 153 (Glu) of SEQ ID NO:5, i.e., a fragment of the extracellular domain terminating ten amino acids upstream of the transmembrane region. The resulting PCR products were digested with SpeI and BglII restriction enzymes.

A DNA encoding the Fc region of a human IgG1 antibody (to be fused to the 4-1BB-encoding sequence) was isolated as follows. SEQ ID NO:14 and SEQ ID NO:15 present the nucleotide and encoded amino acid sequences of a human IgG1 Fc polypeptide-encoding DNA inserted into the polylinker (multiple cloning site) of a pBluescript®SK cloning vector (Stratagene Cloning Systems, La Jolla, Calif.). Amino acids 1–13 of SEQ ID NO: 15 are encoded by the polylinker segment of the vector, and amino acids 14 (Glu) through 245 (Lys) constitute the Fc polypeptide. An Fc-encoding DNA fragment 699 base pairs in length was derived by cleaving the recombinant pBluescript®SK vector with BglII (the recognition site for which comprises nucleotides 47–52 of SEQ ID NO: 14) and SpeI (which cleaves in the polylinker downstream of the inserted Fc sequence).

The Fc fragment and the murine 4-1BB extracellular domain fragment isolated by PCR above were cloned into an SpeI-cleaved Smag 4 vector in a three-way ligation. The Smag 4 vector comprises a murine interleukin-7 (IL-7) leader sequence inserted into the mammalian high expression vector pDC201 (described in Sims et al., *Science* 241:585, 1988, and in PCT application WO 89/03884), which is capable of replication in *E. coli*. *E. coli* cells were transfected with the ligation mixture and the desired recombinant vector (comprising the Fc-encoding DNA joined to the C-terminus of the 4-1BB-encoding DNA via the BglII sites) was isolated therefrom.

The gene fusion encoding the soluble 4-1BB/Fc fusion protein was excised by digesting the recombinant Smag 4 vector with BamHI. The fragment encoding the fusion protein was isolated, the ends were filled in using the Klenow fragment of DNA polymerase I, and the resulting blunt-ended fragment was ligated into a SalI cleaved (blunt ended) dephosphorylated HAV-EO vector.

The gene fusion was transferred to the HAV-EO vector (described by Dower et al., *J. Immunol.* 142:4314; 1989) in order to improve expression levels. The HAV-EO vector is a derivative of pDC201 and allows for high level expression in CV-1/EBNA cells. The CV-1/EBNA cell line (ATCC 10478) was derived by transfecting the African green monkey kidney cell line CV-1 (ATCC CCL-70) with a gene encoding Epstein-Barr virus nuclear antigen-1 (EBNA-1), as described by McMahan et al. (*EMBO J.* 10:2821,1991). The CV-1/EBNA cells constitutively express EBNA-1 driven from the human cytomegalovirus (CMV) intermediate-early enhancer/promoter. The EBNA-1 gene allows for episomal replication of expression vectors such as HAV-EO that contain the EBV origin of replication.

The recombinant HAV-EO vector containing the 4-1 BB/Fc gene fusion was transfected into CV-1/EBNA cells using standard techniques. The transfected cells transiently expressed and secreted a 4-1BB/Fc fusion protein into the culture supernatant, which was harvested after one week of cultivation. The 4-1BB/Fc fusion protein was purified by protein G affinity chromatography. More specifically, one liter of culture supernatant, containing the 4-1BB/Fc fusion protein, was passed over a solid phase protein G column, and the column was washed thoroughly with phosphate-buffered saline (PBS). The adsorbed fusion protein was eluted with 50 mM glycine buffer, pH 3. Purified fusion protein was brought to pH 7 with 2 M Tris buffer, pH 9. Silver-stained SDS gels of the purified 4-1BB/Fc fusion protein showed it to be >98% pure.

Purified 4-1BB/Fc fusion protein was radioiodinated with $^{125}$I using a commercially available solid phase reagent (IODO-GEN, Pierce Chemical Co., Rockford, Ill.). In this procedure, 5 μg of IODO-GEN were plated at the bottom of a 10×75 mm glass tube and incubated for twenty minutes at 4° C. with 75 μl of 0.1M sodium phosphate, pH 7.4 and 20 μl (2 mCi) Na$^{125}$I. The solution was then transferred to a second glass tube containing 5 μg of 4-1BB/Fc in 45 μl PBS (phosphate buffered saline) and this reaction mixture was incubated for twenty minutes at 4° C. The reaction mixture was fractionated by gel filtration on a 2 ml bed volume of Sephadex® G-25 (Sigma), and then equilibrated in RPMI 1640 medium containing 2.5% (v/v) bovine serum albumin (BSA), 0.2% (v/v) sodium azide and 20 mM Hepes, pH 7.4 binding medium. The final pool of $^{125}$I-4-1BB/Fc was diluted to a working stock solution of $1 \times 10^{-7}$M in binding medium and stored for up to one month at 4° C. without detectable loss of receptor binding activity.

Approximately 50%–60% label incorporation was observed. Radioiodination yielded specific activities in the range of $1 \times 10^{15}$ to $5 \times 10^{15}$ cpm/nmole (0.42–2.0 atoms of radioactive iodine per molecule of protein). SDS polyacrylamide gel electrophoresis (SDS-PAGE) revealed a single labeled polypeptide consistent with expected values. The labeled fusion protein was greater than 98% trichloroacetic acid (TCA) precipitable, indicating that the $^{125}$I was covalently bound to the protein.

EXAMPLE 2

Isolation of cDNA Encoding Human 4-1BB

A human cDNA library was screened with a murine 4-1BB DNA probe in an effort to isolate cDNA encoding a human 4-1BB by cross-species hybridization. The degree of homology between murine 4-1BB and human 4-1BB DNA was not known prior to isolation and sequencing of human 4-1BB DNA by the following procedure.

A fragment of the murine 4-1BB DNA of SEQ ID NO:5 was isolated by polymerase chain reaction (PCR) using conventional procedures. The template was cDNA synthesized using a first strand cDNA synthesis kit (Stratagene Cloning Systems, La Jolla, Calif.) on RNA isolated from the induced murine T cell clone BD14-20 (see example 1). The 5' primer was the oligonucleotide presented as SEQ ID NO:9 and described in example 1. The 3' primer was the following oligonucleotide:

5' CAGACTAGTTCACTCTGGAGTCACAG
AAATG 3'                                          (SEQ ID NO:11)

This oligonucleotide comprises an SpeI site (double underline) and a sequence (underlined) that is complementary to nucleotides 510–528 of SEQ ID NO:5 (murine 4-1BB). The amplified PCR products (comprising nucleotides 70–528 of the murine 4-1BB sequence of SEQ ID NO:5) were ligated into a SmaI-digested pBLUESCRIPT®SK cloning vector (Stratagene Cloning Systems, La Jolla, Calif.). E. coli cells were transfected with the ligation mixture, and the desired recombinant vector was recovered. The murine 4-1BB DNA insert was excised by digesting the recombinant vector with NotI and EcoRI. The excised DNA was labeled with $^{32}$P using a conventional random priming technique.

The labeled murine 4-1BB DNA fragment was used to screen a human cDNA library that was constructed as described by Park et al. (*Blood* 74:56, 1989). Briefly, the cDNA library was derived from poly A$^+$ RNA isolated from human peripheral blood T-lymphocytes (purified by E rosetting) that had been activated for 18 hours with phytohemagglutinin (PHA) and phorbol myristate acetate (PMA). Blunt-ended cDNA was methylated and EcoR1 linkers were attached, followed by ligation to λgt10 arms and packaging into phage λ extracts (Stratagene Cloning Systems, La Jolla, Calif.) according to the manufacturer's instructions.

Hybridization was conducted at 37° C. in 50% formamide, followed by washing in 2×SSC, 0.1% SDS at 55° C. The cDNA insert of a hybridizing clone was isolated and sequenced. The nucleotide and encoded amino acid sequences of this human 4-1BB cDNA are presented in SEQ ID NO:7 and SEQ ID NO:8.

The human 4-1BB protein comprises an N-terminal signal peptide (amino acids −23 to −1 of SEQ ID NO:8), an extracellular domain comprising amino acids 1–163, a transmembrane region comprising amino acids 164–190, and a cytoplasmic domain comprising amino acids 191–232. The human 4-1BB of SEQ ID NO:7 is 60% identical to murine 4-1BB at the amino acid level, and 71% identical at the DNA level.

EXAMPLE 3

Preparation of Human 4-1BB/Fc Fusion Protein for Use in Screening Clones

This example illustrates construction of an expression vector encoding a fusion protein comprising the extracellular domain of human 4-1BB fused to the N-terminus of an Fc region polypeptide derived from a human IgG1 antibody. The fusion protein was used for detecting clones encoding a human 4-1BB ligand.

A DNA fragment encoding a soluble human 4-1BB was isolated by PCR using the human 4-1BB cDNA synthesized in example 2 as a template. The 5' primer was the following oligonucleotide:

5' ATAGCGGCCGCTGCCAGATTTCATCATG
GGAAAC 3'                                         (SEQ ID NO:12)

This oligonucleotide comprises a NotI site (double underlined) and a segment (underlined) corresponding to nucleotides 106–128 of SEQ ID NO:7.

The 3' primer was the following oligonucleotide:

5' ACAAGATCTGGGCTC
CTGCGGAGAGTGTCCTGGCTCTCTC 3'   (SEQ ID NO:13)

The oligonucleotide comprises a Bgl II site (double underlined) and a segment (underlined) complementary to nucleotides 653–677 of SEQ ID NO:7. The segment with a dotted underline is complementary to nucleotides 41–46 of SEQ ID NO:14 and serves to replace the codons for the first two amino acids of the Fc polypeptide (amino acids 14 and 15 of SEQ ID NO:14), which are upstream of the BglII site.

A DNA fragment encoding an antibody Fc region polypeptide was isolated by cleaving a recombinant vector comprising Fc-encoding DNA in pBLUESCRIPT®SK (described in example 1) with BglII and NotI. BglII cleaves near the 5' end of the Fc DNA, as described in example 1, and NotI cleaves in the polylinker of the vector downstream of the inserted Fc-encoding DNA.

In a 3-way ligation, the soluble human 4-1BB polypeptide-encoding DNA isolated by PCR above and the Fc-encoding BglII/NotI fragment were ligated into a NotI-digested expression vector pDC406 (described in McMahan et al., *EMBO J.*, 10:2821, 1991). *E. coli* cells were transformed with the ligation mixture and the desired recombinant vector was recovered. The fusion protein encoded by this vector comprised amino acids −23 to 163 of SEQ ID NO:8 (a soluble human 4-1BB polypeptide consisting of the signal peptide and the entire extracellular domain) followed by amino acids 14–245 of SEQ ID NO:15 (Fc polypeptide). CV1-EBNA cells (described in example 1) were transfected with the recombinant vector and cultured to produce and secrete the soluble human 4-1BB/Fc fusion protein. The fusion protein was purified by protein G affinity chromatography for use in identifying clones expressing human 4-1BB ligand, as described in example 5 below.

EXAMPLE 4

Isolation of Murine 4-1BB Ligand cDNA

This example describes the isolation of cDNA encoding a murine 4-1BB ligand (4-1BB-L) using a direct expression cloning technique. The procedure was as follows.

Several cell lines were screened for the ability to bind the radioiodinated murine 4-1BB/Fc fusion protein described in Example 1. Briefly, quantitative binding studies were performed according to standard methodology, and Scatchard plots were derived for the various cell lines. A clonal cell line designated EL4 6.1C10 was identified as expressing approximately 1500 molecules of a 4-1BB/Fc-binding protein per cell, with an affinity binding constant of approximately $2 \times 10^9$ $M^{-1}$. The EL4 6.1C10 cell line was derived from a subclone designated EL4 6.1 by using a cell sorter to enrich for a cell population expressing high levels of murine type I Interleukin-1 receptor, as described in U.S. Pat. No. 4,968,607. EL4 6.1 had been derived from a mouse thymoma cell line EL-4 (ATCC TIB 39) as described by MacDonald et al. (*J. Immunol.* 135:3944, 1985) and Lowenthal and MacDonald (*J. Exp. Med.* 164:1060, 1986).

A cDNA library was derived from the EL4 6.1C10 cell line using a library construction technique substantially similar to that described by Ausubel et al., eds., *Current Protocols in Molecular Biology*, Vol. 1, (1987). Total RNA was extracted from the EL4 6.1C10 cell line, poly (A)⁺ mRNA was isolated by oligo dT cellulose chromatography, and double-stranded cDNA was made substantially as described by Gubler et al., *Gene* 25:263 (1983). Briefly, poly(A)⁺ mRNA fragments were converted to RNA-cDNA hybrids by reverse transcriptase using random hexanucleotides as primers. The RNA-cDNA hybrids were then converted into double-stranded cDNA fragments using RNAse H in combination with DNA polymerase I. The resulting double-stranded cDNA was blunt-ended with T4 DNA polymerase, ligated into SmaI-cleaved, dephosphorylated expression vector pDC201 (described in Sims et al., *Science* 241:585, 1988, and in PCT application WO 89/03884), and transformed into competent *E. coli* DH5α cells.

Plasmid DNA was isolated from pools consisting of approximately 2,000 clones of transformed *E. coli* per pool. The isolated plasmid DNA was transfected into a sub-confluent layer of COS cells using DEAE-dextran followed by chloroquine treatment substantially according to the procedures described in Luthman et al. (*Nucl. Acids Res.* 11:1295, 1983) and McCutchan et al. (*J. Natl. Cancer Inst.* 41:351, 1986). Briefly, COS cells were maintained in complete medium (Dulbecco's modified Eagles' media containing 10% (v/v) fetal calf serum, 50 U/ml penicillin, 50 U/ml streptomycin, and 2 mM L-glutamine and were plated to a density of approximately $2 \times 10^5$ cells/well in single-well chambered slides (Lab-Tek). The slides were pre-treated with 1 ml human fibronectin (10 μg/ml PBS) for 30 minutes followed by a single washing with PBS. Media was removed from the monolayer of adherent cells and replaced with 1.5 ml complete medium containing 66.6 μM chloroquine sulfate. About 0.2 ml of a DNA solution (2 μg DNA, 0.5 mg/ml DEAE-dextran in complete medium containing chloroquine) was added to the cells and the mixture was incubated at 37° C. for about five hours. Following incubation, media was removed and the cells were shocked by addition of complete medium containing 10% DMSO (dimethylsulfoxide) for 2.5–20 minutes. Shocking was followed by replacement of the solution with fresh complete medium. The cells were grown in culture to permit transient expression of the inserted DNA sequences. These conditions led to an 80% transfection frequency in surviving COS cells.

After 48–72 hours in culture, monolayers of transfected COS cells were assayed by slide autoradiography for expression of a protein that binds the radioiodinated murine 4-1BB/Fc fusion protein prepared in Example 1. The slide autoradiography technique was essentially as described by Gearing et al. (*EMBO J.*, 8:3667, 1989). Briefly, the transfected COS cells were washed once with binding medium (RPMI 1640 containing 25 mg/ml bovine serum albumin (BSA), 2 mg/ml sodium azide, 20 mM HEPES pH 7.2, and 50 mg/ml nonfat dry milk) and incubated for 2 hours at 4° C. in binding medium containing $1 \times 10^{-9}$ M $^{125}$I-4-1BB/Fc fusion protein. After incubation, cells in the chambered slides were washed three times with binding medium, followed by two washes with PBS, (pH 7.3) to remove unbound radiolabeled fusion protein.

The cells were fixed by incubating in 10% glutaraldehyde in PBS (30 minutes at room temperature), washed twice in PBS and air-dried. The slides were dipped in Kodak GTNB-2 photographic emulsion (6×dilution in water) and exposed in the dark for four days at room temperature in a light-proof box. The slides were developed in Kodak D 19 developer, rinsed in water and fixed in Agfa G433C fixer. The slides were individually examined under a microscope at 25×40×magnification. Positive slides showing cells expressing 4-1BB ligand were identified by the presence of autoradiographic silver grains against a light background.

One pool containing approximately 2120 individual clones was identified as potentially positive for binding the 4-1BB/Fc fusion protein. The pool was broken down into smaller pools of approximately 250 colonies, from which DNA was isolated and transfected into COS-7 cells. The transfectants were screened by slide autoradiography as described above. Three positive pools were identified. Plasmid DNA isolated from individual colonies corresponding to the three positive pools was transfected into COS cells and screened by the same procedure.

A single clone encoding a protein that binds murine 4-1BB/Fc was isolated. Plasmid DNA was isolated from the clone, and the nucleotide sequence of the cDNA insert in the recombinant vector was determined. The cloned cDNA was found to encode a novel protein, a murine 4-1BB ligand (4-1BB-L) protein of the present invention. The nucleotide sequence of the isolated murine 4-1BB-L cDNA and the amino acid sequence encoded thereby are presented in SEQ ID NO: 1 and SEQ ID NO:2. *E. coli* DH5α cells transformed with a recombinant vector comprising the murine 4-1BB-L-encoding cDNA of SEQ ID NO:1 in the mammalian expression vector pDC201 were deposited with the American Type Culture Collection, Rockville, Md., on Sep. 5, 1991, under accession no. ATCC 68682. The murine 4-1BB-L is a type II protein comprising a cytoplasmic domain (amino acids 1–82 of SEQ ID NO: 1); a transmembrane region (amino acids 83–103 of SEQ ID NO:1); and an extracellular domain (amino acids 104–309 of SEQ ID NO:1).

EXAMPLE 5

Isolation of cDNA Encoding a Human 4-1BB Ligand

Different cell lines were screened by flow cytometry for the ability to bind the human 4-1BB/Fc (hu 4-1BB/Fc) fusion protein prepared in Example 3. Cells were initially incubated with hu4-1BB/Fc (10 µg/ml), followed by biotinylated goat anti-human IgG, Fc-specific (Jackson ImmunoResearch Laboratories, West Grove, Pa.) and finally streptavidin-phycoerythrin (Becton-Dickinson). Flow cytometry was performed using a FACScan (Becton-Dickinson) and data were collected on $10^4$ viable cells. An alloreactive $CD4^+$ human T cell clone designated PL1 stimulated with an anti-CD3 antibody exhibited 4-1BB/Fc binding. The receptor binding was detectable 30 minutes after stimulation and peaked 2–4 hours post-stimulation.

Since peak production of mRNA would precede peak production of the 4-1BB-binding protein translated therefrom, total RNA was isolated from the PL1 cells 90 minutes after stimulation, and poly($A^+$) RNA was isolated by oligo(dT) cellulose chromatography. cDNA was synthesized on the poly(A)$^+$ RNA template using oligo(dT) primers and a cDNA synthesis kit (Pharmacia Biotech, Inc., Piscataway, N.J.). The resulting double-stranded cDNA was ligated into the BglII site of the mammalian expression vector pDC410 by a BglII adaptor method similar to that described by Haymerle et al. (*Nucl. Acids Res.* 14:8615, 1986).

The pDC410 vector is similar to pDC406 (McMahan et al., *EMBO J.*, 10:2821, 1991). In pDC410, the EBV origin of replication of pDC406 is replaced by DNA encoding the SV40 large T antigen (driven from an SV40 promoter). The pDC410 multiple cloning site (mcs) differs from that of pDC406 in that it contains additional restriction sites and three stop codons (one in each reading frame). A T7 polymerase promoter downstream of the mcs facilitates sequencing of DNA inserted into the mcs. *E. coli* strain DH5α cells were transfected with the cDNA library in pDC410.

Plasmid DNA was isolated from the transformed *E. coli* cells, pooled, (each pool consisting of plasmid DNA from approximately 1000 individual colonies) and transfected into a sub-confluent layer of CV-1 EBNA cells (described in example 1). The transfection procedure was the DEAE-dextran followed by chloroquine treatment technique essentially as described in Luthman et al., *Nucl. Acids Res.* 11:1295 (1983), McCutchan et al., *J. Natl. Cancer Inst.* 41:351 (1986). Prior to transfection, the CV1-EBNA cells were plated in single-well chambered slides (Lab-Tek) and grown in culture for two to three days to permit transient expression of the inserted DNA sequences.

The transfected cells then were assayed by slide autoradiography for expression of 4-1BB-L. The assay procedure was similar to that described in example 4, except that the transfected cells were incubated with two reagents. The cells were first washed with binding medium containing nonfat dry milk (BM-NFDM) and incubated with the human 4-1BB/Fc fusion protein prepared in Example 3, in non-radiolabeled form (1 µg/ml in BM-NFDM) for one hour at room temperature. After washing three times with BM-NFDM, cells were incubated with 40 ng/ml $^{125}$I-mouse anti-human Fc antibody (a 1:50 dilution) for one hour at room temperature. The mouse anti-human Fc antibody was obtained from Jackson Immunoresearch Laboratories, Inc, West Grove, Pa., and radiolabeled by the chloramine T method. After washing three times with BM-NFDM and twice with PBS, cell were fixed in glutaraldehyde and slides were processed as described in example 4.

The pool appearing to be most strongly positive was broken down into smaller pools. DNA from the smaller pools was transfected into CV1-EBNA cells and screened by slide autoradiography as described above. Positive pools were identified, and DNA from individual colonies corresponding to the positive pools was screened by the foregoing procedure. Two individual clones expressing 4-1BB-L proteins were isolated. The nucleotide sequence of the human 4-1BB-L cDNA insert of one of the clones (clone 7A) and the amino acid sequence encoded thereby is presented in SEQ ID NO:3 and SEQ ID NO:4. This human 4-1BB-L protein comprises a cytoplasmic domain (amino acids 1–25 of SEQ ID NO:4), a transmembrane region (amino acids 26–46), and an extracellular domain (amino acids 47–252).

The human 4-1BB-L amino acid sequence of SEQ ID NO:3 is about 33% identical to the murine 4-1BB-L amino acid sequence of SEQ ID NO:1, and the nucleotide sequences are about 50% identical. The recombinant vector of clone 7A, i.e., human 4-1BB-L cDNA in vector pDC410, designated hu4-1BB-L (7A)/pDC410, was deposited in *E.coli* DH5α with the American Type Culture Collection, Rockville, Md. on Apr. 16, 1993, under accession number ATCC 69285.

EXAMPLE 6

Expression of Biologically Active Soluble 4-1BB-L in Mammalian Cells

Soluble 4-1BB-L was expressed in a monkey kidney cell line designated CV-1 (ATCC CCL 70). The expressed protein was biologically active in that it bound a 4-1BB/Fc fusion protein.

The soluble 4-1BB-L was produced as follows. DNA encoding amino acids 106 through 309 of the murine 4-1BB-L of SEQ ID NO:1 was isolated by PCR using oligonucleotide primers based on the nucleotide sequence presented in SEQ ID NO:1. The amplified DNA was inserted into the mammalian expression vector designated HAV-EO (described in example 1). cDNA encoding a heterologous (murine interleukin-7) leader peptide, described in U.S. Pat. No. 4,965,195 which is hereby incorporated by reference, was fused to the N-terminus of the 4-1BB-L cDNA to promote secretion of the soluble 4-1BB-L from the host cells. CV-1cells were transformed with the resulting recombinant expression vector by conventional techniques.

The transformed CV-1 cells were cultured to permit expression and secretion of the soluble 4-1BB-L into the supernatant. Various concentrations of the supernatant were tested in a competitive binding assay for the ability to inhibit binding of soluble murine 4-1BB/Fc to EL4 6.1C10 cells. The soluble murine 4-1BB/Fc fusion protein was produced as described in example 1. The murine EL4 6.1C10 cell line expresses cell surface 4-1BB-L, as described in example 4.

The results of the assay, presented in FIG. 1, demonstrate that the soluble murine 4-1BB-L protein expressed in CV-1 cells inhibits binding of a soluble murine 4-1BB/Fc fusion protein to EL4 6.1C10 cells. The soluble 4-1BB-L protein's ability to inhibit binding of 4-1BB/Fc to the cells indicates that the soluble 4-1BB-L is binding to the 4-1BB/Fc.

An expression vector encoding soluble human 4-1BB-L can be substituted for the murine 4-1BB-L-encoding vector in the foregoing procedure. Likewise, human 4-1BB/Fc would be substituted for murine 4-1BB/Fc, and human cells expressing 4-1BB employed in place of murine cells, in the competitive binding assay.

Figure 2:
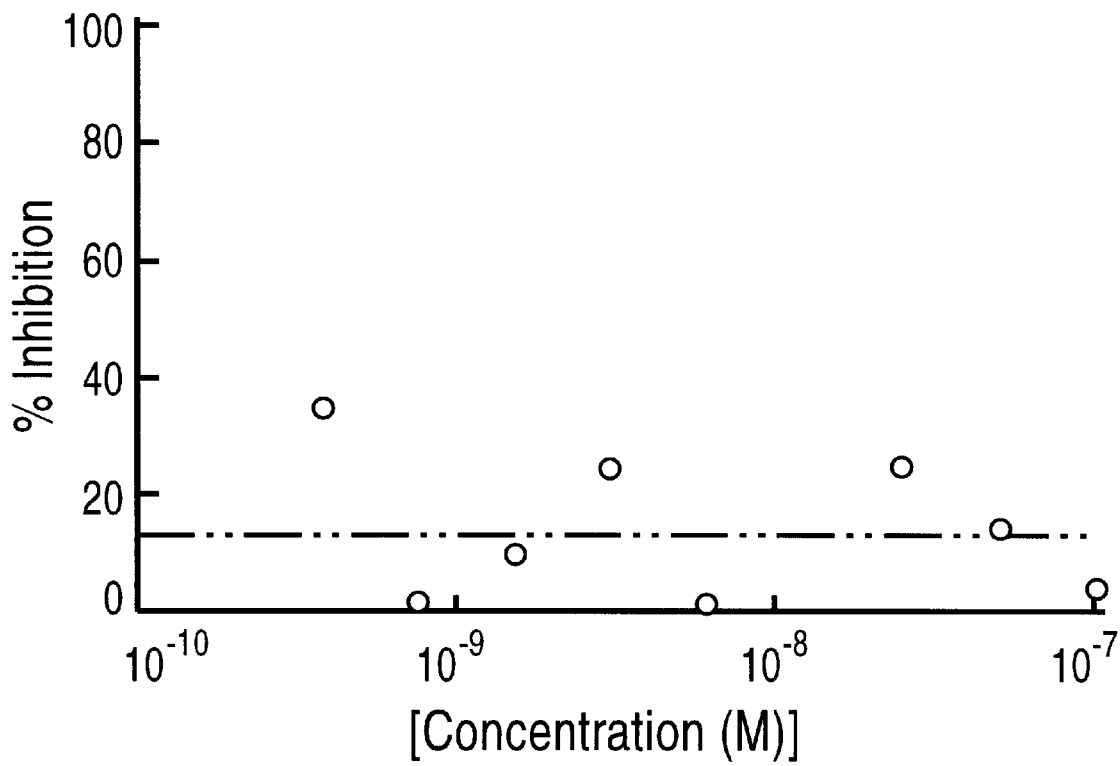
FIG. 2 presents the results of the control experiment described in example 7.

FIG. 2 presents the result of a control experiment in which CV-1 cells were transformed with an "empty" HAV-EO vector (lacking any inserted 4-1BB-L DNA). Supernatant from a culture of the transformed cells did not inhibit binding of 4-1BB/Fc to EL4 6.1C10 cells when tested in the competitive binding assay.

EXAMPLE 7

Expression of Biologically Active Soluble 4-1BB-L in Yeast

Soluble recombinant 4-1BB-L expressed in yeast cells (*Saccharomyces cerevisiae*) was shown to be biologically active in that the expressed protein was able to bind a 4-1BB/Fc fusion protein. The 4-1BB-L protein was produced by inserting cDNA encoding amino acids 106 through 309 of the murine 4-1BB-L of SEQ ID NO:1 (isolated and amplified by PCR) into an expression vector comprising an ADH2 promoter (described above). The expression vector also contained DNA encoding the yeast α-factor leader peptide (described above) fused to the 5' end of DNA encoding a FLAG® peptide DYKDDDDK, which was fused to the 5' end of the 4-1BB-L DNA. The FLAG® octapeptide constitutes an epitope reversibly bound by a particular monoclonal antibody, which facilitates purification of recombinant proteins (4-1BB-L in this case), as described in U.S. Pat. No. 5,011,912. The octapeptide may be removed using bovine mucosal enterokinase, which specifically cleaves at the residue immediately following the DK pairing.

*S. cerevisiae* cells were transformed with the resulting recombinant expression vector by conventional techniques. The transformed cells were cultured to permit expression and secretion of the soluble 4-1BB-L into the supernatant. Various concentrations of the supernatant were tested in a competitive binding assay for the ability to inhibit binding of soluble murine 4-1BB/Fc to EL4 6.1C10 cells. The soluble murine 4-1BB-/Fc fusion protein was produced as described in example 1. Murine EL4 6.1C10 cells express cell surface 4-1BB-L, as described in example 4.

Figure 3:
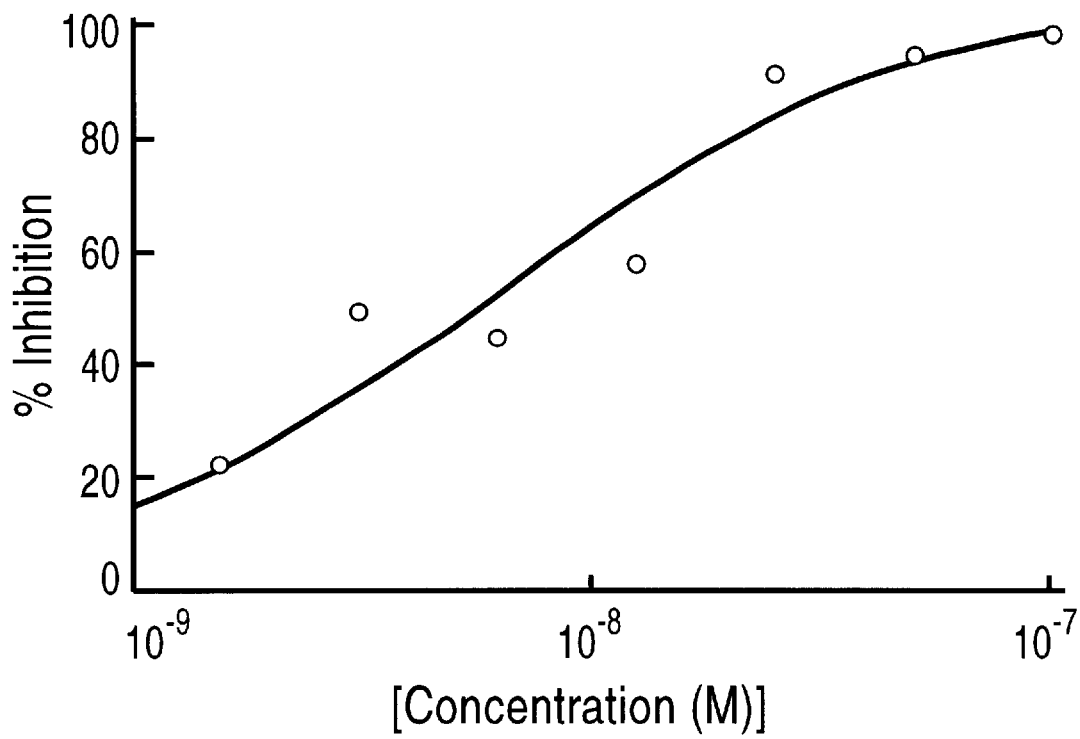
FIG. 3 presents the results of a competition binding assay that demonstrated binding of a murine 4-1BB/Fc fusion protein by a soluble murine 4-1BB-L protein produced in yeast cells. The 4-1BB-L protein was produced as described in example 8.

FIG. 3 presents the results of the competitive binding assay, which demonstrates that the soluble murine 4-1BB-L protein expressed in *S. cerevisiae* cells inhibits binding of the murine 4-1BB/Fc fusion protein to EL4 6.1C10 cells. The 4-1BB-L protein thus is able to bind 4-1BB/Fc. Although recombinant 4-1BB-L can be expressed in yeast cells, mammalian cells are preferred as host cells. The specific activity of 4-1BB-L produced in yeast generally is lower than that of 4-1BB-L produced in mammalian cells such as CV-1.

EXAMPLE 8

Monoclonal Antibodies That Bind 4-1BB-L or 4-1BB

Murine 4-1BB-L or human 4-1BB-L protein may be purified by 4-1BB/Fc affinity chromatography as described above. Full length 4-1BB-L or immunogenic fragments thereof (e.g., the extracellular domain) can be used as an immunogen to generate monoclonal antibodies using conventional techniques, for example, those techniques described in U.S. Pat. No. 4,411,993. Another alternative involves using a soluble 4-1BB-L/Fc fusion protein, comprising the extracellular domain of a 4-1BB-L fused to an antibody Fc polypeptide, as the immunogen.

Briefly, mice are immunized with 4-1BB-L as an immunogen emulsified in complete Freund's adjuvant, and injected subcutaneously or intraperitoneally in amounts ranging from 10–100 μg. Ten to twelve days later, the immunized animals are boosted with additional 4-1BB-L emulsified in incomplete Freund's adjuvant. Mice are periodically boosted thereafter on a weekly to bi-weekly immunization schedule. Serum samples are periodically taken by retro-orbital bleeding or tail-tip excision for testing by dot blot assay or ELISA (Enzyme-Linked Immunosorbent Assay), for antibodies that bind 4-1BB-L.

Following detection of an appropriate antibody titer, positive animals are provided one last intravenous injection of 4-1BB-L in saline. Three to four days later, the animals are sacrificed, spleen cells harvested, and spleen cells are fused to a murine myeloma cell line (e.g., NS1 or Ag 8.653). The latter myeloma cell line is available from the American Type Culture Collection as P3x63Ag8.653 (ATCC CRL 1580). Fusions generate hybridoma cells, which are plated in microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against purified 4-1BB-L by adaptations of the techniques disclosed in Engvall et al., *Immunochem.* 8:871 (1971) and in U.S. Pat. No. 4,703,004. A preferred screening technique is the antibody capture technique described in Beckmann et al., (*J. Immunol.* 144:4212, 1990). Positive hybridoma cells can be injected intraperitoneally into syngeneic BALB/c mice to produce ascites containing high concentrations of anti-4-1BB-L monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to protein A or protein G can be used, as can affinity chromatography based upon binding to 4-1BB-L.

Purified human 4-1BB or immunogenic fragments thereof (e.g., a fragment derived from the -extracellular domain) may be substituted for the 4-1BB-L immunogens in the foregoing procedures. In one embodiment, a soluble human 4-1BB/Fc fusion protein (e.g., as described in example 3) is employed as the immunogen. Monoclonal antibodies that bind human 4-1BB thus are prepared.

EXAMPLE 9

Dimeric Forms of the Inventive Proteins

Preparation of fusion proteins comprising an antibody Fc polypeptide fused to the C-terminus of a soluble human 4-1BB polypeptide (such fusion proteins being referred to as 4-1BB/Fc hereinafter) is described in example 3. Disulfide bonds form between the Fc moieties, as in antibodies, resulting in dimers comprising two 4-1BB/Fc polypeptides. Such dimers may be recovered from cultures of cells expressing the 4-1BB/Fc fusion proteins.

Dimers comprising two 4-1BB-L/Fc polypeptides joined via disulfide bonds may be prepared by analogous procedures. A DNA fragment encoding a soluble 4-1BB-L polypeptide is isolated by procedures described above (e.g., using oligonucleotides that define the desired termini of the fragment as primers in PCR). An expression vector comprising the isolated fragment fused to an Fc-encoding fragment is constructed by procedures analogous to those described in examples 1 and 3. The Fc polypeptide is preferably fused to the N-terminus of the 4-1BB-L polypeptide, however. Dimers of 4-1BB-L/Fc are recovered from cultures of cells transformed with the expression vector.

The dimers preferably are produced in 293 cells (ATCC CRL 1573). The 293 cell line was derived from transformed primary human embryonal kidney cells.

EXAMPLE 10

Cross-Species Reactivity

Inhibition studies were used to investigate cross-species binding of 4-1BB to its ligand. $2.5 \times 10^6$ EL4 6.1 cells (murine thymoma subclone) expressing 1800 mu4-1BB surface ligands/cell were incubated with 0.1 nM $^{125}$I-mu4-1BB/Fc ($1 \times 10^{15}$ cpm/mmole) and serially diluted, unlabeled human or murine 4-1BB/Fc in a total volume of 150 pi binding media for 2 hours at 4° C. Duplicate aliquots were microfuged through a phthalate oil mixture in 400 μl plastic tubes (essentially as described in Smith et al., Cell 73:1349, 1993) to separate bound and free 4-1BB/Fc. The tubes were cut, and top (free) and bottom (bound) 4-1BB/Fc counted. Nonspecific binding was determined by inclusion of a 200-fold molar excess of unlabeled mu4-1BB/Fc.

Unlabeled mu4-1BB/Fc completely inhibited $^{125}$I-mu4-1BB/Fc binding to native surface mu4-1BB-L. Unlabeled hu4-1BB/Fc, however, showed no detectable competition with $^{125}$I-mu4-1BB/Fc for binding to native murine ligand.

Cross-species binding was also assessed qualitatively with the sensitive slide autoradiography assay. Consistent with the inhibition studies, hu4-1BB/Fc did not bind recombinant mu4-1BB-L expressed on the surface of CV-1cells, and no binding of mu4-1BB/Fc to CV-1 cells expressing hu4-1BB-L was detected. Thus, there appears to be no significant ligand/receptor cross-reactivity between human and mouse species.

EXAMPLE 11

Expression of Human 4-1BB-L mRNA

Northern blot analysis demonstrated the presence of multiple size classes of hu4-1BB-L mRNA transcripts. 4-1BB-L message was absent in resting PL-1 cells, but was present within 30 minutes after stimulation with immobilized anti-CD3 mAb, peaking at approximately one hour after stimulation. A hybridoma designated OKT3 that produces an anti-CD3 monoclonal antibody is available from ATCC under the designation CRL 8001.

Transcripts were also observed in a variety of other human cell lines such as the EBV-transformed human B cell line MP-1, the monocytic cell line THP-1, the Mo-7E megakaryocytic cell line and the neuroblastoma SK-N-SH. Human 4-1BB-L transcripts were absent in RNA isolated from the AML cell line KG-1. A Northern blot of RNAs from various human tissues (Clonetech, Palo Alto, Calif.) was also probed, which demonstrated the expression of 4-1BB-L transcripts in brain, placenta, lung, skeletal muscle and kidney. Transcripts were either not present, or present in very low amounts in heart, liver and pancreas.

EXAMPLE 12

Expression of Endogenous Human 4-1BB

A monoclonal antibody reactive with human 4-1BB was generated using the soluble human 4-1BB/Fc fusion protein of example 3 to immunize BALB/cJ mice, and screening for reactivity with hu4-1BB/Fc but not human IgG1 by ELISA. This monoclonal antibody (IgG1 isotype) was employed to analyze the expression of hu4-1BB on a variety of primary human cells and cell lines. Northern blot analysis was also conducted. Human 4-1BB protein or message (detected by the antibody or the blot, respectively) was detected for activated primary T-cells, the alloreactive CD4⁺ T-cell clone PL-1, EBV transformed B cell lines, the pro-monocytic cell line U937, and resting and activated peripheral blood monocytes.

EXAMPLE 13

Effect of 4-1 BB-L on T-Cell Proliferation (a) Peripheral Blood T-Cells

The ability of human 4-1BB-L to costimulate T-cell proliferation was assessed in a 3 day tritiated thymidine-incorporation assay. The assay procedure was generally as described by Goodwin et al. (Cell 73:447, 1993). Briefly, human peripheral blood T-cells were isolated and cultured with a titration of fixed CV-1/EBNA cells transfected with either empty vector or an expression vector containing DNA encoding full length hu4-1BB-L, in the presence of suboptimal PHA (0.1%) as a costimulus. After 3 days, cultures were pulsed with [$^3$H] thymidine and incorporated radioactivity was assessed 6 hours later.

Figure 4:
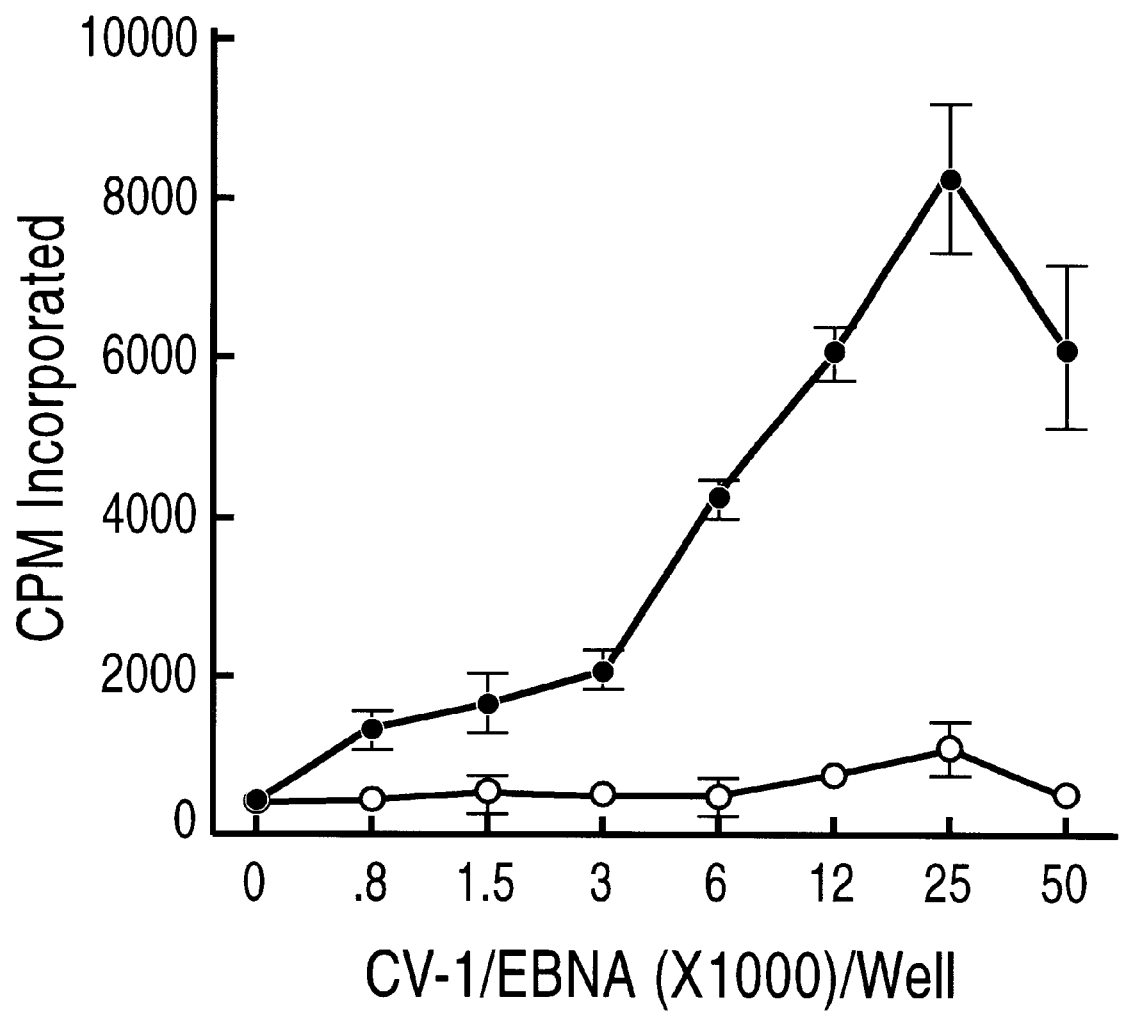
FIG. 4 presents the results of an assay described in example 13, in which cells expressing recombinant human 4-1BB-L were demonstrated to costimulate T-cell proliferation. Purified T cells were cultured with a titration of fixed CV-1/EBNA cells that were transfected with either empty vector (open circles) or vector containing hu4-1BB-L DNA (closed circles) in the presence of suboptimal PHA (0.1%). After 3 days, cultures were pulsed with [3H] thymidine and incorporated radioactivity was assessed 6 hours later. Data are representative of four experiments.

The results are shown in FIG. 4. The open circles represent the CV-1/EBNA cells transfected with the empty expression vector, and closed circles represent the CV-1/EBNA cells transfected with the hu4-1BB-L-encoding expression vector.

The CV-1/EBNA cells expressing recombinant hu4-1BB-L markedly enhanced T-cell proliferation induced by sub-optimal PHA, whereas control CV-1/EBNA cells had no effect. The hu4-1BB-L had no effect on T-cell proliferation in the absence of a costimulus.

Another thymidine incorporation assay was conducted as described above, except that $10^4$ CV-1/EBNA cells were employed, rather than a titration. Additional controls included soluble hu4-1BB/Fc plus the cells expressing hu4-1BB-L; and a soluble human p80 tumor necrosis factor receptor (TNF-R)/Fc fusion protein plus the cells expressing hu4-1BB-L. Enhanced T-cell proliferation was again observed for T-cells cultured with PHA and cells expressing hu4-1BB-L. This enhancement of T-cell proliferation was specifically blocked by hu4-1BB/Fc but not by TNF-R/Fc.

(b) T-Cell Clone

The effect of hu4-1BB-L on a long term cultured T-cell clone was also analyzed. Chronically activated T-cells, such as long-term grown T-cell clones (TCC), are induced to undergo programmed cell death when stimulated with mitogens such as anti-CD3 mAb or PHA in the absence of antigen-presenting cells (Wesselborg et al., J. Immunol. 150:4338, 1993). Since TCC express 4-1BB, we assessed the effect of 4-1BB-L on the growth of the alloreactive CD4+ human T-cell clone designated PL-1.

PL-1 cells were cultured for 3 days in the presence or absence of suboptimal PHA (0.1%) as costimulus and CV-1 cells transfected with either empty vector (control) or the expression vector containing DNA encoding full length human 4-1BB-L. Viability was determined by trypan blue exclusion.

4-1BB-L had no effect on PL-1 viability or growth in the absence of a costimulus. However, in the presence of PHA, addition of CV-1/EBNA cells expressing 4-1BB-L reduced the viability of PL-1 cells from 57% to 31%. 4-1BB-L thus enhanced activation-induced cytolysis of the PL-1 cells.

What is claimed is:

1. An antibody that specifically binds a polypeptide selected from the group consisting of:
   (a) a polypeptide encoded by a DNA consisting of nucleotides 53–979 of SEQ ID NO:1 or nucleotides 4–765 of the sequence of SEQ ID NO:3;
   (b) a polypeptide encoded by a DNA which, due to the degeneracy of the genetic code, encodes a polypeptide encoded by a DNA of (a).

2. An antibody of claim 1, wherein said antibody is a monoclonal antibody.

3. An antibody that specifically binds a polypeptide consisting of amino acids 1–254 of SEQ ID NO:4, amino acids 49–254 of SEQ ID NO:4, amino acids 1–309 of SEQ ID NO:2, or amino acids x-309 of SEQ ID NO:2, wherein x is selected from the group consisting of 104, 105 and 106.

4. An antibody of claim 3, wherein said antibody is a monoclonal antibody.

* * * * *